US006706875B1

(12) United States Patent
Goldberg et al.

(10) Patent No.: US 6,706,875 B1
(45) Date of Patent: Mar. 16, 2004

(54) SUBSTRATE PREPARATION PROCESS

(75) Inventors: Martin Goldberg, San Jose, CA (US); Martin Diggelman, Arlesheim (CH); Earl Hubbell, Mountain View, CA (US); Glenn McGall, Mountain View, CA (US); Nam Quoc Ngo, Campbell, CA (US); MacDonald Morris, San Jose, CA (US); Mel Yamamoto, Fremont, CA (US); Jennifer Tan, Newark, CA (US); Richard P. Rava, San Jose, CA (US)

(73) Assignee: Affyemtrix, Inc., Santa Clara, CA (US)

( * ) Notice: Subject to any disclaimer, the term of this patent is extended or adjusted under 35 U.S.C. 154(b) by 108 days.

(21) Appl. No.: 09/716,507

(22) Filed: Nov. 20, 2000

Related U.S. Application Data

(63) Continuation of application No. 09/244,568, filed on Feb. 4, 1999, now Pat. No. 6,307,042, which is a continuation of application No. 08/634,053, filed on Apr. 17, 1996, now Pat. No. 5,959,098.

(51) Int. Cl.[7] .................. C07H 21/00; C07H 21/02; C07H 21/04; C12Q 1/68
(52) U.S. Cl. .................. 536/25.3; 435/6; 536/22.1; 536/23.1; 536/26.6
(58) Field of Search .................. 435/6; 536/22.1, 536/23.1, 25.3, 26.6

(56) References Cited

U.S. PATENT DOCUMENTS

| | | |
|---|---|---|
| 4,016,855 A | 4/1977 | Mimata |
| 4,401,796 A | 8/1983 | Itakura |
| 4,458,066 A | 7/1984 | Caruthers et al. |
| 4,500,707 A | 2/1985 | Caruthers et al. |
| 4,507,433 A | 3/1985 | Miller et al. |
| 5,143,854 A | 9/1992 | Pirrung et al. |
| 5,202,231 A | 4/1993 | Drmanac et al. |
| 5,242,974 A | 9/1993 | Holmes |
| 5,384,261 A | 1/1995 | Winkler et al. |
| 5,424,186 A * | 6/1995 | Fodor et al. ............ 435/6 |
| 5,445,934 A | 8/1995 | Fodor et al. |
| 5,489,678 A | 2/1996 | Fodor et al. |

FOREIGN PATENT DOCUMENTS

| | | | |
|---|---|---|---|
| GB | 2182336 | * | 5/1987 |
| WO | WO 92/10092 | | 6/1992 |
| WO | WO 93/090668 | | 5/1993 |
| WO | WO 94/10128 | | 5/1994 |
| WO | WO 95/00530 | | 1/1995 |
| WO | WO 95/33846 | | 12/1995 |

OTHER PUBLICATIONS

Atkinson et al., "Solid–Phase Synthesis of Oligodeoxyribonucleotides by the Phosphitetriester Method," IRL Press, Gait, ed., Washington, D.C., Chapt. 3, pp. 35–81 (1984).

Barnett et al., "Debenzoylation of N–Benzoylnucleoside Derivatives with Ethylendiamine–Phenol," *Tetrahedron Lett.*, 22:991–994 (1981).

Beaucage et al., "Deoxynucleoside Phosphoramidites—A New Class of Key Intermediates for Deoxypolynucleotide Synthesis," *Tetrahedron Lett.*, 22(20):1859–1862 (1981).

Caruthers et al., "New Methods for Synthesizing Deoxynucleotides," *Genetic Eng.*, 4:1–17 (1982).

Feldman et al., "Gray Code Masks for Sequencing by Hybridization," *Genomics*, 23:233–235 (1994).

(List continued on next page.)

*Primary Examiner*—Jezia Riley
(74) *Attorney, Agent, or Firm*—Banner & Witcoff, Ltd.

(57) ABSTRACT

The present invention provides novel processes for the large scale preparation of arrays of polymer sequences wherein each array includes a plurality of different, positionally distinct polymer sequences having known monomer sequences The methods of the invention combine high throughput process steps with high resolution photolithographic techniques in the manufacture of polymer arrays.

52 Claims, 20 Drawing Sheets

(List continued on next page.)

| | | | |
|---|---|---|---|
| 5,492,806 | A | 2/1996 | Drmanac et al. |
| 5,510,270 | A | 4/1996 | Fodor et al. |
| 5,525,464 | A | 6/1996 | Drmanac et al. |
| 5,527,681 | A | 6/1996 | Holmes |
| 5,545,531 | A | 8/1996 | Rava et al. |
| 5,556,752 | A | 9/1996 | Lockhart et al. |
| 5,624,711 | A | 4/1997 | Sundberg et al. |
| 5,631,734 | A | 5/1997 | Stern et al. |
| 5,639,603 | A | 6/1997 | Dower et al. |
| 5,667,972 | A | 9/1997 | Drmanac et al. |
| 5,695,940 | A | 12/1997 | Drmanac et al. |
| 5,700,637 | A | 12/1997 | Southern |
| 5,723,289 | A * | 3/1998 | Eaton et al. .................. 435/6 |
| 5,764,518 | A | 6/1998 | Collins |
| 5,837,832 | A | 11/1998 | Chee et al. |
| 5,945,334 | A | 8/1999 | Besemer et al. |
| 6,225,625 | B1 | 5/2001 | Pirrung et al. |

OTHER PUBLICATIONS

Froehler et al., "Synthesis of DNA via Deoxynucleotides H–Phosphonate Intermediates," *Nucleic Acids Res.*, 14(13):5399–5407 (1986).

Froehler et al., "Nucleoside H–Phosphonates: Valuable Intermediates in the Synthesis of Deoxyoligonucleotides," *Tetrahedron Lett.*, 27(4):469–472 (1986).

Guo et al., "Direct Fluorescence Analysis of Genetic Polymorphisms by Hybridization with Oligonucleotide Arrays on Glass Supports," *Nucleic Acids Res.*, 22(24):5456–5465 (1994).

Hogrefe et al., "Deprotection of Methylphosphonate Oligonucleotides Using a Novel One–Pot Procedure," *Nucleic Acids Res.*, 21(9):2031–2038 (1993).

Jones, "Preparation of Protected Deoxyribonucleosides," *Oligonucleotide Synthesis: A Practical Approach*, IRL Press, Gait, ed., Washington, D.C., Chapter 2 (1984).

Matteuci et al, "Synthesis of Deoxyoligonucleotides on a Polymer Support," *J. Am. Chem. Soc.*, 103(11):3185–3191 (1981).

McGillis, "Lithography," *VLSI Technology, McGraw–Hill*, Chapt. 7, pp. 267–301 (1983).

Pease et al., "Light–Generated Oligonucleotide Arrays for Rapid DNA Sequence Analysis," *Proc. National Acad. Sci. USA*, 91:5022–5026 (1994).

Polushin et al., "Rapid Deprotection Procedures for Synthesis Oligonucleotides," *N.A.R. Symp. Ser.*, No. 24, pp. 49–50 (1991).

Reichmanis et al., "O–Nitrobenzyl Photochemistry: Solution vs. Solid–State Behavior," *J. Polymer Sci. Polymer Chem., Ed.*, 23:1–8 (1985).

Sinha et al., "β–cyanoethyl N, N–dialkylamino/N–morpholinomonochloro Phosphoamidites, New Phosphyitylating Agent Facilitating Ease of Deprotection and Work–Up of Synthesized Oligonucleotides," *Tetrahedron Lett.*, 24(52):5843–5846 (1983).

Sinha et al., "Polymer Support Oligonucleotide Synthesis XVIII: Use of β–cyanoethyl–N, N–dialkylamino/N–morpholinomonochloro Phosphoamidite of Deoxynucleosides for the Synthesis of DNA Fragments Simplyifying Deprotection and Isolation of the Final Product," *Nucl. Acids Res.*, 12(11):4539–4557 (1984).

Sproat et al., "Solid–Phase Synthesis of Oligodeoxyribonucleotides by the Phosphotriester Method," *Oligonucleotide Synthesis: A Practical Approach IRL Press*, Gait, ed., Washington, D.C., Chapt. 4, pp. 83–115 (1984).

Young and Davis, "Efficient Isolation of Genes by Using Antibody Probes," *Proc. National. Acad. Sci. USA*, 80:1194 (1983).

* cited by examiner

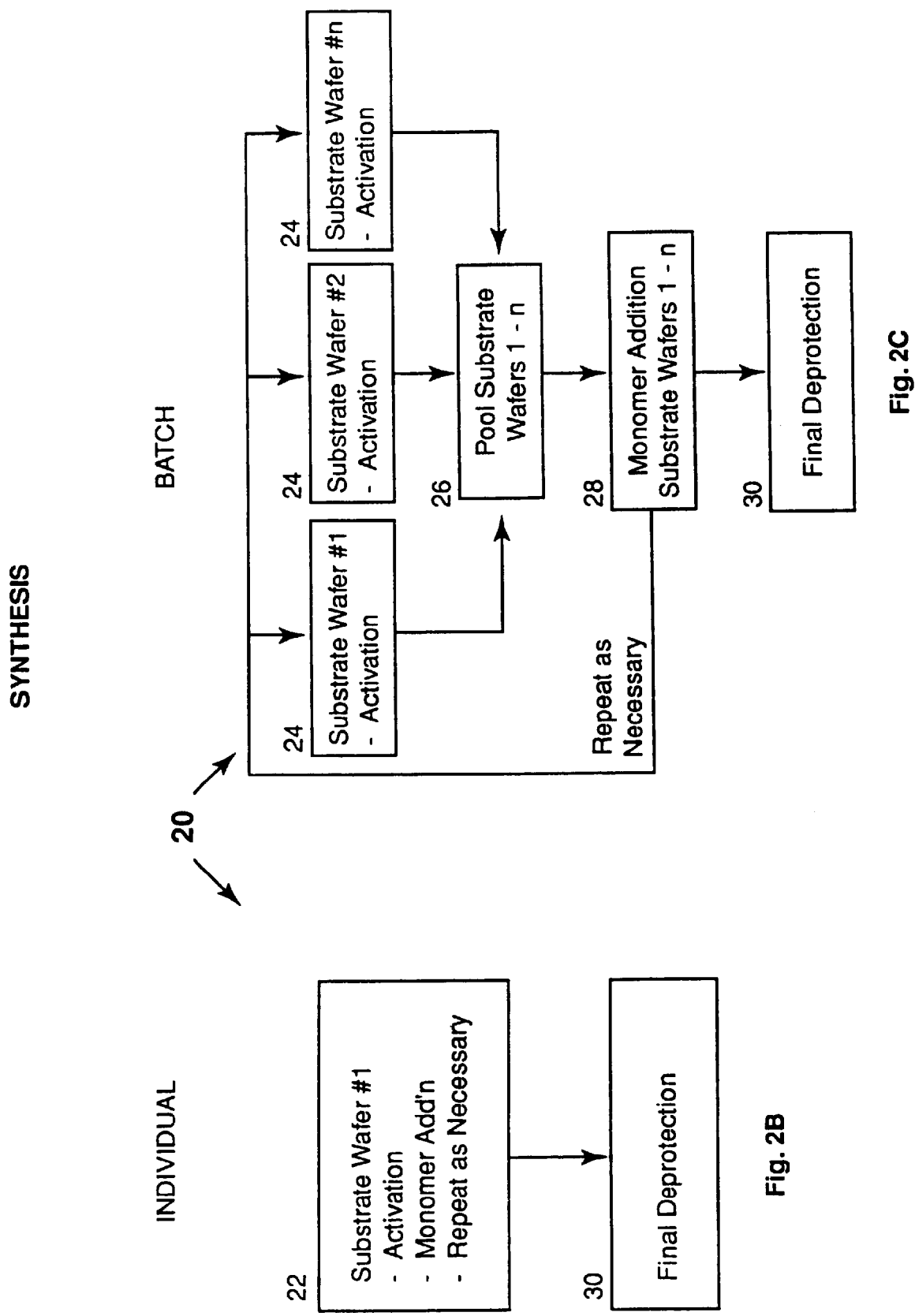

SUBSTRATE PREPARATION PROCESS

This application is a continuation of U.S. patent application Ser. No. 09/244,568, filed Feb. 4, 1999, now U.S. Pat. No. 6,307,042; which in turn is a continuation of U.S. patent application Ser. No. 08/634,053, filed Apr. 17, 1996, now U.S. Pat. No. 5,959,098.

BACKGROUND OF THE INVENTION

Methods for synthesizing a variety of different types of polymers are well known in the art. For example, the "Merrifield" method, described in Atherton et al., "Solid Phase Peptide Synthesis," IRL Press, 1989, which is incorporated herein by reference for all purposes, has been used to synthesize peptides on a solid support. In the Merrifield method, an amino acid is covalently bonded to a support made of an insoluble polymer or other material. Another amino acid with an alpha protecting group is reacted with the covalently bonded amino acid to form a dipeptide. After washing, the protecting group is removed and a third amino acid with an alpha protecting group is added to the dipeptide. This process is continued until a peptide of a desired length and sequence is obtained.

Methods have also been developed for producing large arrays of polymer sequences on solid substrates. These large "arrays" of polymer sequences have wide ranging applications and are of substantial importance to the pharmaceutical, biotechnology and medical industries. For example, the arrays may be used in screening large numbers of molecules for biological activity, i.e., receptor binding capability. Alternatively, arrays of oligonucleotide probes can be used to identify mutations in known sequences, as well as in methods for de novo sequencing of target nucleic acids.

Of particular note, is the pioneering work described in U.S. Pat. No. 5,143,854 (Pirrung et al.) and PCT Application No. 92/10092 disclose improved methods of molecular synthesis using light directed techniques. According to these methods, light is directed to selected regions of a substrate to remove protecting groups from the selected regions of the substrate. Thereafter, selected molecules are coupled to the substrate, followed by additional irradiation and coupling steps. By activating selected regions of the substrate and coupling selected monomers in precise order, one can synthesize an array of molecules having any number of different sequences, where each different sequence is in a distinct, known location on the surface of the substrate.

These arrays clearly embody the next step in solid phase synthesis of polymeric molecules generally, and polypeptides and oligonucleotides, specifically. Accordingly, it would be desirable to provide methods for preparation of these arrays, which methods have high throughput, high product quality, enhanced miniaturization and lower costs. The present invention meets these and other needs.

SUMMARY OF THE INVENTION

The present invention generally provides novel processes for the efficient, large scale preparation of arrays of polymer sequences wherein each array includes a plurality of different, positionally distinct polymer sequences having known monomer sequences. In one embodiment, the methods of the present invention provide for the cleaning and stripping of substrate wafers to remove oil and dirt from the surface, followed by the derivatization of the wafers to provide photoprotected functional groups on the surface. Polymer sequences are then synthesized on the surface of the substrate wafers by selectively exposing a plurality of selected regions on the surface to an activation radiation to remove the photolabile protecting groups from the functional groups and contacting the surface with a monomer containing solution to couple monomers to the surface in the selected regions. The exposure and contacting steps are repeated until a plurality of polymer arrays are formed on the surface of the substrate wafer. Each polymer array includes a plurality of different polymer sequences coupled to the surface of the substrate wafer in a different known location. The wafers are then separated into a plurality of individual substrate segments, each segment having at least one polymer array formed thereon, and packaged in a cartridge whereby the surface of said substrate segment having the polymer array formed thereon is in fluid contact with the cavity.

In another embodiment, the present invention provides methods of forming polymer arrays by providing a substrate having a first surface coated with functional groups protected with a photolabile protecting group, and a second surface having a layer that includes one or more of an index matching compound, a light absorbing compound and an antireflective compound. The method then provides for the sequential activation and coupling of monomers in different selected regions of the first surface of the substrate to form a plurality of different polymer sequences in different known locations on the surface of the substrate, by directing an activation radiation at the first surface of the substrate.

In yet another embodiment, the present invention provides a method of forming a plurality of polymer arrays using a batch process. In particular, this method comprises the steps of activating a plurality of substrate wafers by exposing selected regions on each of a plurality of substrate wafers then contacting them with a monomer containing solution in a batch.

In a further embodiment, the present invention provides a method of synthesizing polymers on substrates by first derivatizing the substrate with an aminoalkyltrialkoxysilane.

In an additional embodiment, the present invention provides a method for forming an array of polymers on a substrate using light-directed synthesis wherein the exposing step comprises directing an activation radiation at selected regions on the surface of said substrate by shining the activation radiation through a photolithographic mask having transparent regions and opaque regions where the transparent regions are smaller than the selected regions. As a result, the activation radiation shone through the transparent regions in the mask is diffracted to expose the selected regions.

The present invention also provides methods of forming arrays of polymer sequences having enhanced synthesis efficiencies through the incorporation of monomers which have lipophilic chemical groups coupled thereto.

The present invention also provides methods of forming polymer arrays using the above-described methods, but wherein the deprotection and coupling steps in adjacent selected regions of the substrate surface are aligned to minimize differences in synthesis steps between adjacent regions.

In still another embodiment, the present invention provides polymer arrays and methods of forming them on a tubular substrate by the sequential activation of and coupling of monomers to selected segments of the tubular substrate surface.

In an additional embodiment, the present invention provides methods of photoprotecting functional groups that are coupled to solid supports by exposing the functional group to a photoprotecting group transfer agent having the formula:

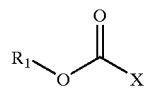

wherein $R_1$ is a photolabile protecting group and X is a leaving group.

BRIEF DESCRIPTION OF THE DRAWINGS

FIGS. 2A–C are flow diagrams illustrating the overall process of substrate preparation. FIG. 2A is a flow dagram illustrating the overall process. FIGS. 2B and 2C are flow diagrams of the synthesis steps for individual and batch processes, respectively.

FIG. 9C illustrates the contrast difference from a top view of the plots while FIG. 9D shows a side view.

DESCRIPTION OF THE PREFERRED EMBODIMENT

I. Definitions

Figure 1:
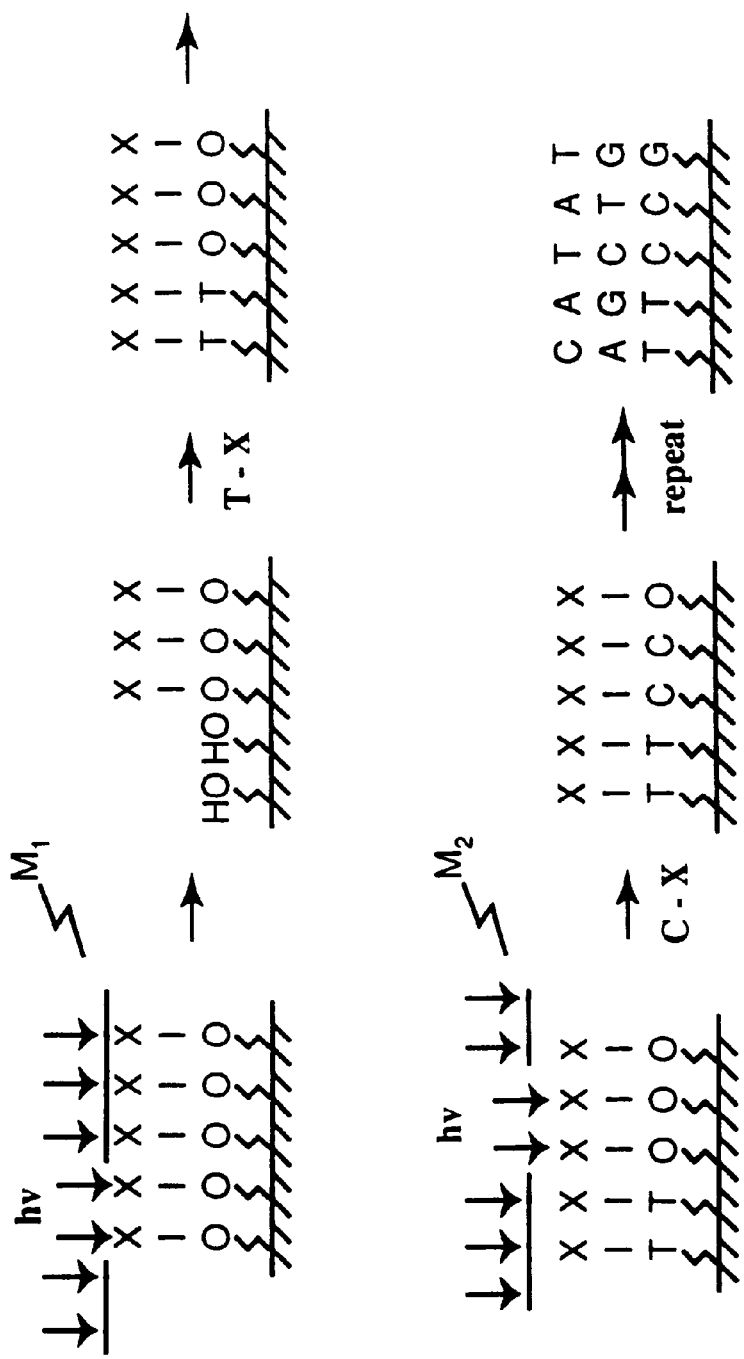
FIG. 1 schematically illustrates light directed oligonucleotide synthesis using photolithographic methods.

Probe: A probe, as defined herein, is a surface-immobilized molecule that is recognized by a particular target. These may also be referred to as ligands. Examples of probes encompassed by the scope of this invention include, but are not limited to, agonists and antagonists of cell surface receptors, toxins and venoms, viral epitopes, hormone receptors, peptides, peptidomimetics, enzymes, enzyme substrates, cofactors, drugs, lectins, sugars, oligonucleotides, nucleic acids, oligosaccharides, proteins or monoclonal antibodies, natural or modified, e.g., reshaped, chimeric, etc.

Array: An array is a preselected collection of different polymer sequences or probes which are associated with a surface of a substrate. An array may include polymers of a given length having all possible monomer sequences made up of a specific basis set of monomers, or a specific subset of such an array. For example, an array of all possible oligonucleotides of length 8 includes 65,536 different sequences. However, as noted above, an oligonucleotide array also may include only a subset of the complete set of probes. Similarly, a given array may exist on more than one separate substrate, e.g., where the number of sequences necessitates a larger surface area in order to include all of the desired polymer sequences.

Functional group: A functional group is a reactive chemical moiety present on a given monomer, polymer or substrate surface. Examples of functional groups include, e.g., the 3' and 5' hydroxyl groups of nucleotides and nucleosides, as well as the reactive groups on the nucleobases of the nucleic acid monomers, e.g., the exocyclic amine group of guanosine, as well as amino and carboxyl groups on amino acid monomers.

Monomer/Building block: A monomer or building block is a member of the set of smaller molecules which can be joined together to form a larger molecule or polymer. The set of monomers includes but is not restricted to, for example, the set of common L-amino acids, the set of D-amino acids, the set of natural or synthetic amino acids, the set of nucleotides (both ribonucleotides and deoxyribonucleotides, natural and unnatural) and the set of pentoses and hexoses. As used herein, monomer refers to any member of a basis set for synthesis of a larger molecule. A selected set of monomers forms a basis set of monomers. For example, the basis set of nucleotides includes A, T (or U), G and C. In another example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

Feature: A feature is defined as a selected region on a surface of a substrate in which a given polymer sequence is contained. Thus, where an array contains, e.g., 100,000 different positionally distinct polymer sequences on a single substrate, there will be 100,000 features.

Edge: An edge is defined as a boundary between two features on a surface of a substrate. The sharpness of this edge, in terms of reduced bleed over from one feature to another, is termed the "contrast" between the two features.

Protecting group: A protecting group is a material which is chemically bound to a reactive functional group on a monomer unit or polymer and which protective group may be removed upon selective exposure to an activator such as a chemical activator, or another activator, such as electromagnetic radiation or light, especially ultraviolet and visible light. Protecting groups that are removable upon exposure to electromagnetic radiation, and in particular light, are termed "photolabile protecting groups."

II. Abbreviations

| | |
|---|---|
| ACN | Acetonitrile |
| Bz | Benzoyl |
| CE | β-cyanoethyl |
| CEP | Cyanoethylphosphoramidite |
| DCM | dichloromethane |
| DIEA | Diiminoethylamine |
| dG | Deoxyguanosine |
| DMAP | Dimethylaminopyridine |
| DMC | N,N-dimethylcarbamoyl |
| DMF | Dimethylformamide |
| DMT | 4,4'-Dimethoxytrityl |
| DPC | Diphenylcarbamoyl |
| HOAT | 1-Hydroxy-7-azabenzotriazole |
| HOBT | 1-hydroxybenzotriazole |
| Ibu | Isobutyryl |
| MeNP | α-methyl-o-nitropiperonyl |
| MeNPOC | α-methyl-o-nitropiperonyloxycarbonyl |
| MeNV | α-methyl-o-nitroveratryl |
| MeNVOC | α-methyl-o-nitroveratryloxycarbonyl |
| MMT | 4-Methoxytrityl |
| NMI | n-methylimidazole |
| NMP | n-methylpyrollidinone |
| NP | o-Nitropiperonyl |
| NPE | 2-(p-nitrophenyl)ethyl |
| NPSE | 2-(p-nitrophenylsulfonyl)ethyl |
| NV | o-Nitroveratryl |
| NPOC | o-Nitropiperonyloxycarbonyl |
| NVOC | o-Nitroveratryloxycarbonyl |
| PAC | Phenoxyacetyl |
| PYMOC | 1-Pyrenylmethyloxycarbonyl |
| SSPE | Saline, Sodium phosphate, EDTA Buffer |
| TEA | Triethylamine |
| THF | Tetrahydrofuran |

III. Process Overview

Figure 2A:
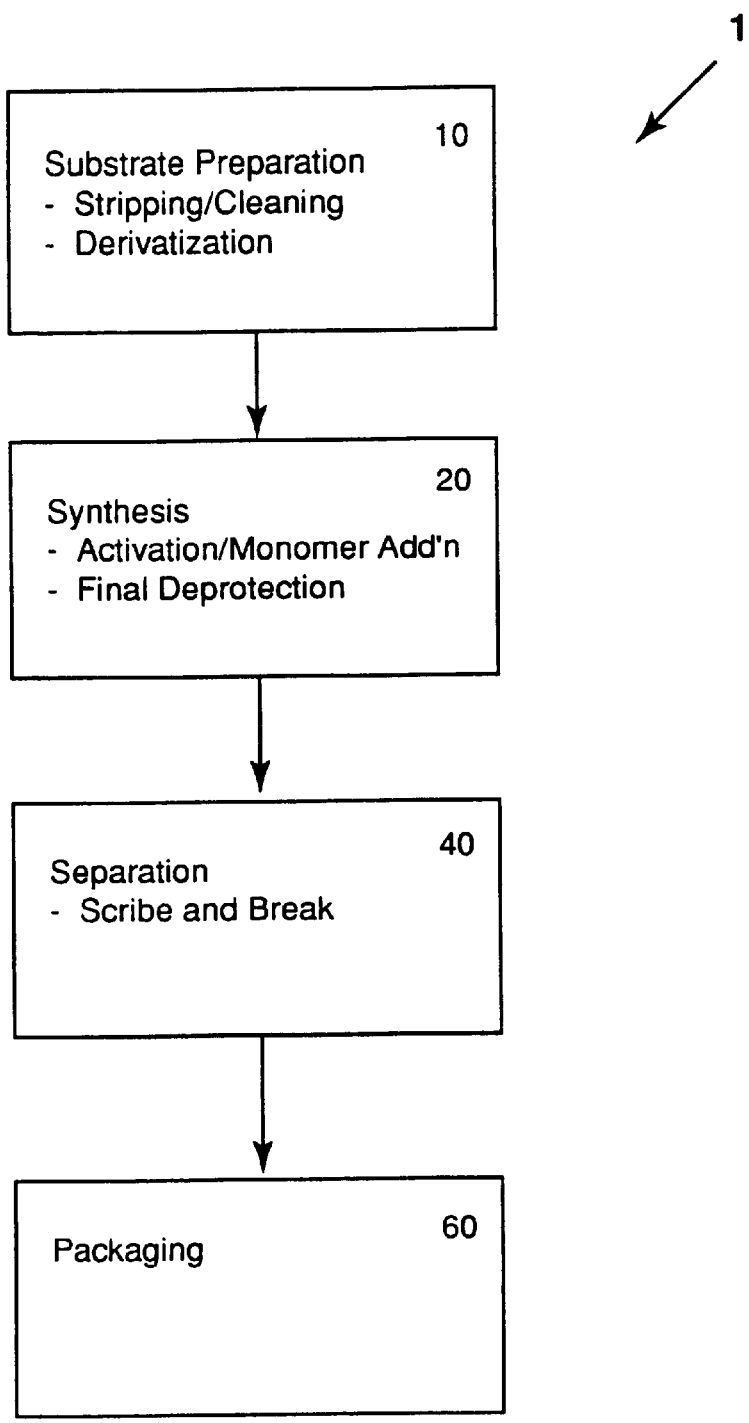

The present invention generally provides processes and devices for reproducibly and efficiently preparing arrays of polymer sequences on solid substrates. The overall process is illustrated in FIG. 2A. Generally, the process 1 begins with a series of substrate preparation steps 10 which may include such individual processing steps as stripping cleaning and derivatization of the substrate surface to provide uniform reactive surfaces for synthesis. The polymer sequences are then synthesized on the substrate surface in the synthesis step 20. Following polymer synthesis, the substrates are then separated into individual arrays 40, and assembled in cartridges that are suitable for ultimate use 60. In alternate embodiments, the present invention also provides for the synthesis of the polymer sequences on the substrate surface using either an individual or batch process mode. A comparison of these two synthesis modes is shown in FIG. 2B. In the individual processing mode, the activation and monomer addition steps are combined in a single unit operation 22. For example, a single substrate wafer is placed in a reactor system where it is first subjected to an activation step to activate selected regions of the substrate. The substrate is then contacted with a first monomer which is coupled to the activated region. Activation and coupling steps are repeated until the desired array of polymer sequences is created. The arrays of polymer sequences are then subjected to a final deprotection step 30.

In the batch processing mode, a number of substrate wafers are subjected to an activating step 24. The activated substrate wafers are then pooled 26 and subjected to a monomer addition step 28. Each substrate wafer is then subjected individually to additional activation steps followed by pooling and monomer addition. This is repeated until a desired array of polymer sequences is formed on the substrate wafers in a series of individual arrays. These arrays of polymer sequences on the substrate wafers are then subjected to a final deprotection step 30.

IV. Substrate Preparation

The term "substrate" refers to a material having a rigid or semi-rigid surface. In many embodiments, at least one surface of the substrate will be substantially flat or planar, although in some embodiments it may be desirable to physically separate synthesis regions for different polymers with, for example, wells, raised regions, etched trenches, or the like. According to other embodiments, small beads may be provided on the surface which may be released upon completion of the synthesis. Preferred substrates generally comprise planar crystalline substrates such as silica based substrates (e.g. glass, quartz, or the like), or crystalline substrates used in, e.g., the semiconductor and microprocessor industries, such as silicon, gallium arsenide and the like. These substrates are generally resistant to the variety of synthesis and analysis conditions to which they may be subjected. Particularly preferred substrates will be transparent to allow the photolithographic exposure of the substrate from either direction.

Silica aerogels may also be used as substrates. Aerogel substrates may be used as free standing substrates or as a surface coating for another rigid substrate support. Aerogel substrates provide the advantage of large surface area for polymer synthesis, e.g., 400 to 1000 $m^2/gm$, or a total useful surface area of 100 to 1000 $cm^2$ for a 1 $cm^2$ piece of aerogel substrate. Such aerogel substrates may generally be prepared by methods known in the art, e.g., the base catalyzed polymerization of $(MeO)_4Si$ or $(EtO)_4Si$ in ethanol/water solution at room temperature. Porosity may be adjusted by altering reaction coondition by methods known in the art.

Individual planar substrates generally exist as wafers which can have varied dimensions. The term "wafer" generally refers to a substantially flat sample of substrate from which a plurality of individual arrays or chips may be fabricated. The term "array" or "chip" is used to refer to the final product of the individual array of polymer sequences, having a plurality of different positionally distinct polymer sequences coupled to the surface of the substrate. The size of a substrate wafer is generally defined by the number and nature of arrays that will be produced from the wafer. For example, more complex arrays, e.g., arrays having all possible polymer sequences produced from a basis set of monomers and having a given length, will generally utilize larger areas and thus employ larger substrates, whereas simpler arrays may employ smaller surface areas, and thus, less substrate.

Typically, the substrate wafer will range in size of from about 1"×1" to about 12"×12", and will have a thickness of from about 0.5 mm to about 5 mm. Individual substrate segments which include the individual arrays, or in some cases a desired collection of arrays, are typically much smaller than the wafers, measuring from about 0.2 cm×0.2 cm to about 5 cm×5 cm. In particularly preferred aspects, the substrate wafer is about 5"×5" whereas the substrate segment is approximately 1.28 cm×1.28 cm. Although a wafer can be used to fabricate a single large substrate segment, typically, a large number of substrate segments will be prepared from a single wafer. For example, a wafer that is 5"×5" can be used to fabricate upwards of 49 separate 1.28 cm×1.28 cm substrate segments. The number of segments prepared from a single wafer will generally vary depending upon the complexity of the array, and the desired feature size.

Although primarily described in terms of flat or planar substrates, the present invention may also be practiced with substrates having substantially different conformations. For example, the substrate may exist as particles, strands, precipitates, gels, sheets, tubing, spheres, containers, capillaries, pads, slices, films, plates, slides, etc. In a preferred alternate embodiment, the substrate is a glass tube or microcapillary. The capillary substrate provides advantages of higher surface area to volume ratios, reducing he amount of reagents necessary for synthesis. Similarly, he higher surface to volume ratio of these capillary substrates imparts more efficient thermal transfer properties. Additionally, preparation of the polymer arrays may be simplified through the use of these capillary based substrates. For example, minimizing differences between the regions on the array, or "cells", and their "neighboring cells" is simplified in that there are only two neighboring cells for any given cell (see discussion below for edge minimization in chip design). Spatial separation of two neighboring cells on an array merely involves the incorporation of a single blank cell, as opposed to full blank lanes as generally used in a flat substrate conformation. This substantially conserves the surface area available for polymer synthesis. Manufacturing design may also be simplified by the linear nature of the substrate. In particular, the linear substrate may be moved down a single mask in a direction perpendicular to the length of the capillary. As it is moved, the capillary will encounter linear reticles (translucent regions of the mask), one at a time, thereby exposing selected regions within the capillary or capillary. This can allow bundling of parallel capillaries during synthesis wherein the capillaries are exposed to thicker linear reticles, simultaneously, for a batch processing mode, or individual capillaries may be placed on a mask having all of the linear reticles lined up so that the capillary can be stepped down the mask in one direction. Subsequent capillaries may be stepped down the mask at least one step behind the previous capillary. This employs an assembly line structure to the substrate preparation process.

As an example, a standard optimization chip for detecting 36 simultaneous mutations using a flat geometry chip and an optimization tiling strategy, is 44×45 features (1980 probes and blanks), with 36 blocks of 40 probes each (1440 probes), plus 15 blanks per block (540 blank probes). A capillary format, however, can incorporate the same number of test probes in a smaller space. Specifically, in a capillary substrate, 36 strings of 40 probes will have only one blank pace separating each probe group (35 blank probes), for a otal of 1475 features.

Finally, linear capillary based substrates can provide the advantage of reduced volume over flat geometries. In particular, typical capillary substrates have a volume in the 1–10 μl range, whereas typical flow cells for synthesizing or screening flat geometry chips have volumes in the range of 100 μl.

A. Stripping and Rinsing

In order to ensure maximum efficiency and accuracy in synthesizing polymer arrays, it is generally desirable to provide a clean substrate surface upon which the various. reactions are to take place. Accordingly, in some processing embodiments of the present invention, the substrate is stripped to remove any residual dirt, oils or other fluorescent materials which may interfere with the synthesis reactions, or subsequent analytical use of the array.

The process of stripping the substrate typically involves applying, immersing or otherwise contacting the substrate with a stripping solution. Stripping solutions may be selected from a number of commercially available, or readily prepared chemical solutions used for the removal of dirt and oils, which solutions are well known in the art. Particularly preferred stripping solutions are composed of a mixture of concentrated $H_2SO_4$ and $H_2O_2$. Such solutions are generally available from commercial sources, e.g., Nanostrip™ from Cyantek Corp. After stripping, the substrate is rinsed with water and in preferred aspects, is then contacted with a solution of NaOH, which results in regeneration of an even layer of hydroxyl functional groups on the surface of the substrate. In this case, the substrate is again rinsed with water, followed by a rinse with HCl to neutralize any remaining base, followed again by a water rinse. The various stripping and rinsing steps may generally be carried out using a spin-rinse-drying apparatus of the type generally used in the semiconductor manufacturing industry.

Gas phase cleaning and preparation methods may also be applied to the substrate wafers using, e.g., $H_2O$ or $O_2$ plasma or reactive ion etching (RIE) techniques that are well known in the art.

B. Derivatization

Following cleaning and stripping of the substrate surface, the surface is derivatized to provide sites or functional groups on the substrate surface for synthesizing the various polymer sequences on that surface. In particular, derivatization provides reactive functional groups, e.g., hydroxyl, carboxyl, amino groups or the like, to which the first monomers in the polymer sequence may be attached. In preferred aspects, the substrate surface is derivatized using silane in either water or ethanol. Preferred silanes include mono- and dihydroxyalkylsilanes, which provide a hydroxyl functional group on the surface of the substrate. Also preferred are aminoalkyltrialkoxysilanes which can be used to provide the initial surface modification with a reactive amine functional group. Particularly preferred are 3-aminopropyltriethoxysilane and 3-aminopropyltrimethoxysilane ("APS"). Derivatization of the substrate using these latter amino silanes provides a linkage that is stable under synthesis conditions and final deprotection conditions (for oligonucleotide synthesis, this linkage is typically a phosphoramidate linkage, as compared to the phosphodiester linkage where hydroxyalkylsilanes are used). Additionally, this amino silane derivatization provides several advantages over derivatization with hydroxyalkylsilanes. For example, the aminoalkyltrialkoxysilanes are inexpensive and can be obtained commercially in high purity from a variety of sources, the resulting primary and secondary amine functional groups are more reactive nucleophiles than hydroxyl groups, the aminoalkyltrialkoxysilanes are less prone to polymerization during storage, and they are sufficiently volatile to allow application in a gas phase in a controlled vapor deposition process (See below).

Additionally, silanes can be prepared having protected or "masked" hydroxyl groups and which possess significant volatility. As such, these silanes can be readily purified by, e.g., distillation, and can be readily employed in gas-phase deposition methods of silanating substrate surfaces. After coating these silanes onto the surface of the substrate, the hydroxyl groups may be deprotected with a brief chemical treatment, e.g., dilute acid or base, which will not attack the substrate-silane bond, so that the substrate can then be used for polymer synthesis. Examples of such silanes include acetoxyalkylsilanes, such as acetoxyethyltrichlorosilane, acetoxypropyltrimethoxysilane, which may be deprotected after application using, e.g., vapor phase ammonia and methylamine or liquid phase aqueous or ethanolic ammonia and alkylamines. Epoxyalkylsilanes may also be used, such as glycidoxypropyltrimethoxysilane which may be deprotected using, e.g., vapor phase HCl, trifluoroacetic acid or the like, or liquid phase dilute HCl.

The physical operation of silanation of the substrate generally involves dipping or otherwise immersing the substrate in the silane solution. Following immersion, the substrate is generally spun as described for the substrate stripping process, i.e., laterally, to provide a uniform distribution of the silane solution across the surface of the substrate. This ensures a more even distribution of reactive functional groups on the surface of the substrate. Following application of the silane layer, the silanated substrate may be baked to polymerize the silanes on the surface of the substrate and improve the reaction between the silane reagent and the substrate surface. Baking typically takes place at temperatures in the range of from 90° C. to 120° C. with 110° C. being most preferred, for a time period of from about 1 minute to about 10 minutes, with 5 minutes being preferred.

In alternative aspects, as noted above, the silane solution may be contacted with the surface of the substrate using controlled vapor deposition methods or spray methods. These methods involve the volatilization or atomization of the silane solution into a gas phase or spray, followed by deposition of the gas phase or spray upon the surface of the substrate, usually by ambient exposure of the surface of the substrate to the gas phase. or spray. Vapor deposition typically results in a more even application of the derivatization solution than simply immersing the substrate into the solution.

The efficacy of the derivatization process, e.g., the density and uniformity of functional groups on the substrate surface, may generally be assessed by adding a fluorophore which binds the reactive groups, e.g., a fluorescent phosphoramidite such as Fluoreprime™ from Pharmacia, Corp., Fluoredite™ from Millipore, Corp. or FAM™ from ABI, and looking at the relative fluorescence across the surface of the substrate.

V. Synthesis

General methods for the solid phase synthesis of a variety of polymer types have been previously described. Methods of synthesizing arrays of large numbers of polymer sequences, including oligonucleotides and peptides, on a single substrate have also been described. See U.S. Pat. Nos. 5,143,854 and 5,384,261 and Published PCT Application No WO 92/10092, each of which is incorporated herein by reference in its entirety for all purposes.

As described previously, the synthesis of oligonucleotides on the surface of a substrate may be carried out using light directed methods as described in., e.g., U.S. Pat. Nos. 5,143,854 and 5,384,261 and Published PCT Application No WO 92/10092, or mechanical synthesis methods as described in U.S. Pat. No. 5,384,261 and Published PCT Application No.93/09668, each of which is incorporated herein by reference. Preferably, synthesis is carried out using light-directed synthesis methods. In particular, these light-directed or photolithographic synthesis methods involve a photolysis step and a chemistry step. The substrate surface, prepared as described herein comprises functional groups on its surface. These functional groups are protected by photolabile protecting groups ("photoprotected"), also as described herein. During the photolysis step, portions of the surface of the substrate are exposed to light or other activators to activate the functional groups within those portions, i.e., to remove photoprotecting groups. The substrate is then subjected to a chemistry step in which chemical monomers that are photoprotected at at least one functional group are then contacted with the surface of the substrate. These monomers bind to the activated portion of the substrate through an unprotected functional group.

Subsequent activation and coupling steps couple monomers to other preselected regions, which may overlap with all or part of the first region. The activation and coupling sequence at each region on the substrate determines the sequence of the polymer synthesized thereon. In particular, light is shown through the photolithographic masks which are designed and selected to expose and thereby activate a first particular preselected portion of the substrate. Monomers are then coupled to all or part of this portion of the substrate. The masks used and monomers coupled in each step can be selected to produce arrays of polymers having a range of desired sequences, each sequence being coupled to a distinct spatial location on the substrate which location also dictates the polymer's sequence. The photolysis steps and chemistry steps are repeated until the desired sequences have been synthesized upon the surface of the substrate.

Basic strategy for light directed synthesis of oligonucleotides on a VLSIPS™ Array is outlined in FIG. 1. The surface of a substrate or solid support, modified with photosensitive protecting groups (X) is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Pease et al., *Proc. Natl. Acad. Sci.* (1994) 91:5022–5026. Since photolithography is used, the process can be readily miniaturized to generate high density arrays of oligonucleotide probes. Furthermore, the sequence of the oligonucleotides at each site is known. Such photolithographic methods are also described in U.S. Pat. Nos. 5,143,854, 5,489,678 and Published PCT Application No. WO 94/10128 each of which is incorporated herein by reference in its entirety for all purposes. In the large scale processes of the present invention, it is typically preferred to utilize photolithographic synthesis methods.

Using the above described methods, arrays may be prepared having all polymer sequences of a given length which are composed of a basis set of monomers. Such an array of oligonucleotides, made up of the basis set of four nucleotides, for example, would contain up to $4^n$ oligonucleotides on its surface, where n is the desired length of the oligonucleotide probe. For an array of 8 mer or 10 mer oligonucleotides, such arrays could have upwards of about 65,536 and 1,048,576 different oligonucleotides respectively. Generally, where it is desired to produce arrays having all possible polymers of length n, a simple binary masking strategy can be used, as described in U.S. Pat. No. 5,143,854.

Alternate masking strategies can produce arrays of probes which contain a subset of polymer sequences, i.e., polymers having a given subsequence of monomers, but are systematically substituted at each position with each member of the basis set of monomers. In the context of oligonucleotide probes, these alternate synthesis strategies may be used to lay down or "tile" a range of probes that are complementary to, and span the length of a given known nucleic acid segment. The tiling strategy will also include substitution of one or more individual positions within the sequence of each of the probe groups with each member of the basis set of nucleotides. These positions are termed "interogation positions." By reading the hybridization attern of the target nucleic acid, one can determine if and where any mutations lie in the sequence, and also determine what the specific mutation is by identifying which base is contained within the interogation position. Tiling methods and strategies are discussed in substantial detail in U.S. patent application Ser. No. 08/143,312 filed Oct. 26, 1993, and incorporated herein by reference in its entirety for all purposes.

Tiled arrays may be used for a variety of applications, such as identifying mutations within a known oligonucleotide sequence or "target". Specifically, the probes on the array will have a subsequence which is complementary to a known nucleic acid sequence, but wherein at least one position in that sequence has been systematically substituted with the other three nucleotides.

Use of photolabile protecting groups during polymer synthesis has been previously reported, as described above. Preferred photolabile protecting groups generally have the following characteristics: they prevent selected reagents from modifying the group to which they are attached; they are stable to synthesis reaction conditions (that is, they remain attached to the molecule); they are removable under conditions that minimize potential adverse effects upon the structure to which they are attached; and, once removed, they do not react appreciably with the surface or surface bound oligomer. In some embodiments, liberated byproducts of the photolysis reaction can be rendered unreactive toward the growing oligomer by adding a reagent that specifically reacts with the byproduct.

The removal rate of the photolabile protecting groups generally depends upon the wavelength and intensity of the incident radiation, as well as the physical and chemical properties of the protecting group itself. Preferred protecting groups are removed at a faster rate and with a lower intensity of radiation. Generally, photoprotecting groups that undergo photolysis at wavelengths in the range from 300 nm to approximately 450 nm are preferred.

Generally, photolabile or photosensitive protecting groups include ortho-nitrobenzyl and ortho-nitrobenzyloxycarbonyl protecting groups. The use of these protecting groups has been proposed for use in photolithography for electronic device fabrication (see, e.g., Reichmanis et al., *J. Polymer Sci. Polymer Chem. Ed.* (1985) 23:1–8, incorporated herein by reference for all purposes).

Examples of additional photosensitive protecting groups which may be used in the light directed synthesis methods herein described, include, e.g., 1-pyrenylmethyloxycarbonyl, α,α-dimethyl-3,5-dimethoxybenzyloxycarbonyl, 4-methoxyphenacyloxycarbonyl, 3'-methoxybenzoinyloxycarbonyl, 3',5'-dimethoxybenzoinyl-oxycarbonyl 2',3'-dimethoxybenzoinyl-oxycarbonyl, 2',3'-(methylenedioxy)benzoinyloxycarbonyl, N-(5-bromo-7-nitroindolinyl)carbonyl 3,5-dimethoxybenzyloxycarbonyl, and α-(2-methyleneanthraquinone)oxycarbonyl.

Particularly preferred photolabile protecting groups for protection of either the 3' or 5'-hydroxyl groups of nucleotides or nucleic acid polymers include the o-nitrobenzyl protecting groups described in Published PCT Application No. WO 92/10092. These photolabile protecting groups include, e.g., nitroveratryloxycarbonyl (NVOC), nitropiperonyl oxycarbonyl (NPOC), α-methyl-nitroveratryloxycarbonyl (MeNVOC), α-methyl-nitropiperonyloxycarbonyl (MeNPOC), 1-pyrenylmethyloxycarbonyl (PYMOC), and the benzylic forms of each of these (i.e., NV, NP, MeNV, MeNP and PYM, respectively), with MeNPOC being most preferred.

Protection strategies may be optimized for different phosphoramidite nucleosides to enhance synthesis efficiency. Examples of such optimized synthesis methods are reported in, e.g., U.S. patent application Ser. No. 08/445,332 filed May 9, 1995. Generally, these optimization methods involve selection of particular protecting groups for protection of the $O^6$ group of guanosine, which can markedly improve coupling efficiencies in the synthesis of guanosine containing oligonucleotides. Similarly, selection of the appropriate protecting group for protection of the $N^2$ group of guanosine can also result in such an improvement, in absence of protection of the $O^6$ group. For example, suitable protecting groups for protection of the $N^2$ group, where the $O^6$ group is also protected, include, e.g., mono- or diacyl protecting groups, triarylmethyl protecting groups, e.g., DMT and MMT, and amidine type protecting groups, e.g., N,N-dialkylformamidines. Particularly preferred protecting groups for the $N_2$ group include, e.g., DMT, DMF, PAC, Bz and Ibu.

Protection of the $O^6$ group will generally be carried out using carbamate protecting groups such as —C(O)NX$_2$, where X is alkyl, or aryl; or the protecting group —CH$_2$CH$_2$Y, where Y is an electron withdrawing group such as cyano, p-nitrophenyl, or alkyl- or aryl-sulfonyl; and aryl protecting groups. In a particularly preferred embodiment, the $O^6$ group is protected using a diphenyl-carbamoyl protecting group (DPC).

Alternatively, improved coupling efficiencies may be achieved by selection of an appropriate protecting group for only the $N^2$ group. For example, where the $N^2$-PAC protecting group is substituted with an Ibu protecting group, a substantial improvement in coupling efficiency is seen, even without protection of the $O^6$ group.

A variety of modifications can be made to the above-described synthesis methods. For example, in some embodiments, it may be desirable to directly transfer or add photolabile protecting groups to functional groups, e.g., NH$_2$, OH, SH or the like, on a solid support. For these methods, conventional peptide or oligonucleotide monomers or building blocks having chemically removable protecting groups are used instead of monomers having photoprotected functional groups. In each cycle of the synthesis procedure, the monomer is coupled to reactive sites on the substrate, e.g., sites deprotected in a prior photolysis step. The protecting group is then removed using conventional chemical techniques and replaced with a photolabile protecting group prior to the next photolysis step.

A number of reagents will effect this replacement reaction. Generally, these reagents will have the following generic structure:

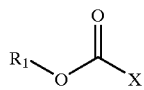

where $R_1$ is a photocleavable protecting group and X is a leaving group, i.e., from the parent acid HX. The stronger acids typically correspond to better leaving groups and thus, more reactive acylating agents.

Examples of suitable leaving groups include a number of derivatives having a range of properties, e.g., relative reactivity, solubility, etc. These groups generally include simple inorganic ions, i.e., halides, $N_3^-$, and the like, as well as compounds having the following structures:

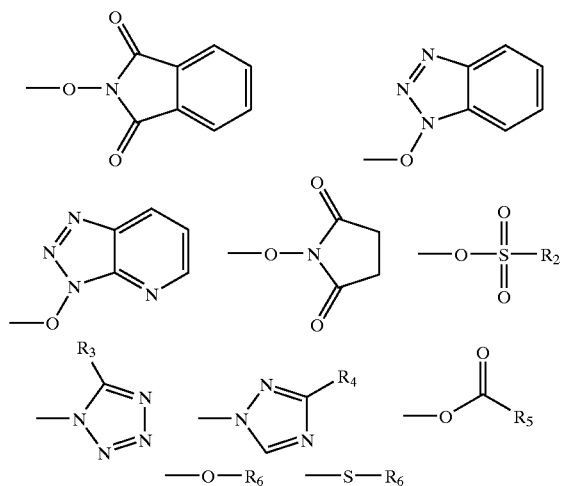

where $R_2$ is alkyl, substituted alkyl or aryl, $R_3$ is hydrogen, alkyl, thioalkyl, aryl; $R_4$ is an electron withdrawing group such as $NO_2$, $SO_2$—$R_2$, or CN; $R_5$ is a sterically hindered alkyl or aryl group such as adamantyl, t-butyl and the like; and $R_6$ is alkyl or aryl substituted with electronegative substituents. Examples of these latter leaving groups include:

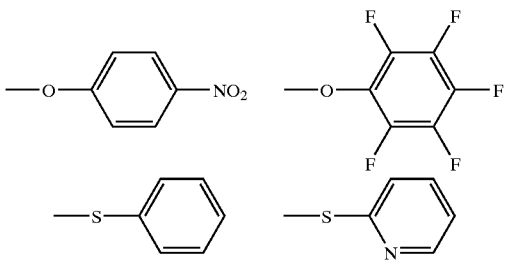

Conditions for carrying out this transfer are similar to those used for coupling reaction in solid phase peptide synthesis, or for the capping reaction in solid phase oligonucleotide synthesis. The solid phase amine, hydroxyl or thiol groups are exposed to a solution of the protecting group coupled to the leaving group, e.g., MeNPOC-X in a nonnucleophilic organic solvent, e.g., DMF, NMP, DCM, THF, ACN, and the like, in the presence of a base catalysts, such as pyridine, 2,6-lutidine, TEA, DIEA and the like. In cases where acylation of surface groups is less efficient under these conditions, nucleophilic catalysts such as DMAP, NMI, HOBT, HOAT and the like, may also be included to accelerate the reaction through the in situ generation of more reactive acylating agents. This would typically be the case where a derivative is preferred for its longer term stability in solution, but is not sufficiently reactive without the addition of one or more of the catalysts mentioned above. On automated synthesizers, it is generally preferable to choose a reagent which can be stored for longer terms as a stable solution and then activated with the catalysts only when needed, i.e., in the reactor system flow cell, or just prior to the addition of the reagent to the flow cell.

In addition to the protection of amine groups and hydroxyl groups in peptide and oligonucleotide synthesis, the reagents and methods described herein may be used to transfer photolabile protecting groups directly to any nucleophilic group, either tethered to a solid support or in solution.

A. Individual Processing

1. Flow Cell/Reactor System

In one embodiment, the substrate preparation process of the present invention combines the photolysis and chemistry steps in a single unit operation. In this embodiment, the substrate wafer is mounted in a flow cell during both the photolysis and chemistry or monomer addition steps. In particular, the substrate is mounted in a reactor system that allows for the photolytic exposure of the synthesis surface of the substrate to activate the functional groups thereon. Solutions containing chemical monomers are then introduced into the reactor system and contacted with the synthesis surface, where the monomers can bind with the active functional groups on the substrate surface. The monomer containing solution is then removed from the reactor system, and another photolysis step is performed, exposing and activating different selected regions of the substrate surface. This process is repeated until the desired polymer arrays are created.

Reactor systems and flow cells that are particularly suited for the combined photolysis/chemistry process include those described in, e.g., U.S. Pat. No. 5,424,186, which is incorporated herein by reference in its entirety for all purposes.

Figure 3A:
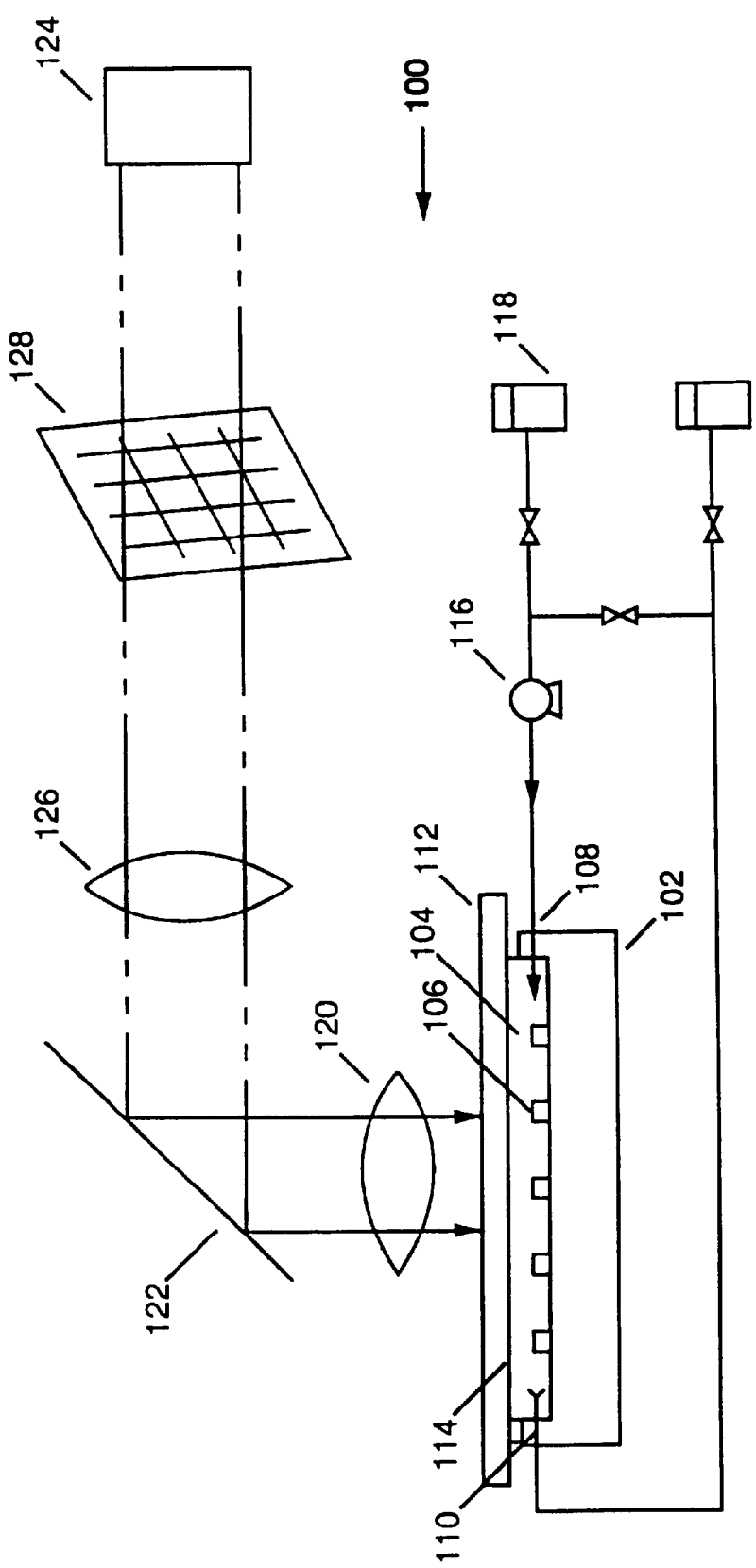
FIGS. 3A and 3B show schematic illustrations of alternate reactor systems for carrying out the combined photolysis/chemistry steps of used in the methods of the present invention.
Figure 3B:
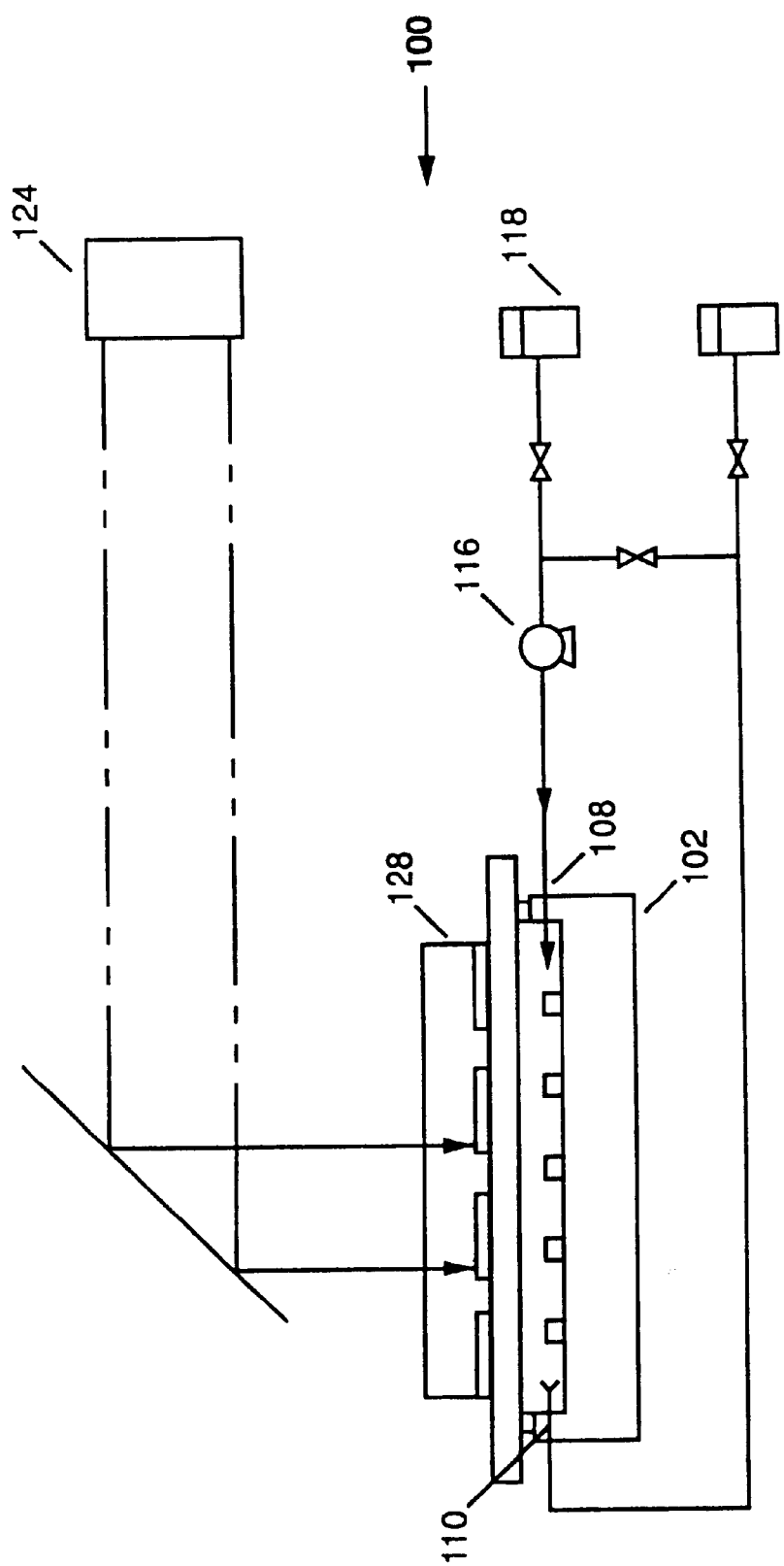

A schematic illustration of a device for carrying out the combined photolysis/chemistry steps of the individual rocess, is shown in FIGS. 3A and 3B. These figures show a cross-sectional view of alternate embodiments of the reactor system 100. Referring first to FIG. 3B, the device includes a flow cell which is made up of a body 102 having a cavity 104 disposed in one surface. The cavity generally includes fluid inlets 108 and outlets 110 for flowing fluid into and through the cavity. The cavity may optionally include ridges 106 on the back surface of the cavity to aid in mixing the fluids as they are pumped into and through the cavity. The substrate 112 is mounted over the cavity whereby the front surface of the substrate wafer 114 (the surface upon which the arrays are to be synthesized) is in fluid communication with the cavity. The device also includes a fluid delivery system in fluid connection with the fluid inlet 108 for delivering selected fluids into the cavity to contact the first surface of the substrate. The fluid delivery system typically delivers selected fluids, e.g., monomer containing solutions, index matching fluids, wash solutions, etc., from one or more reagent reservoirs 118, into the cavity via the fluid inlet 108. The delivery system typically includes a pump 116 and one or more valves to select from the various reagent reservoirs.

For carrying out the photolysis reactions, the device 100 also typically includes a light source 124, as described above. The light source is shown through a photolithographic mask 128 and is directed at the substrate 112. Directing the light source at the substrate may generally be carried out using, e.g., mirrors 122 and/or lenses 120 and 126. Alternatively, as shown in FIG. 3B, the mask 128 may be placed directly over the substrate 112, i.e. immediately adjacent to the substrate, thereby obviating the need for intervening lenses.

Figure 4A:
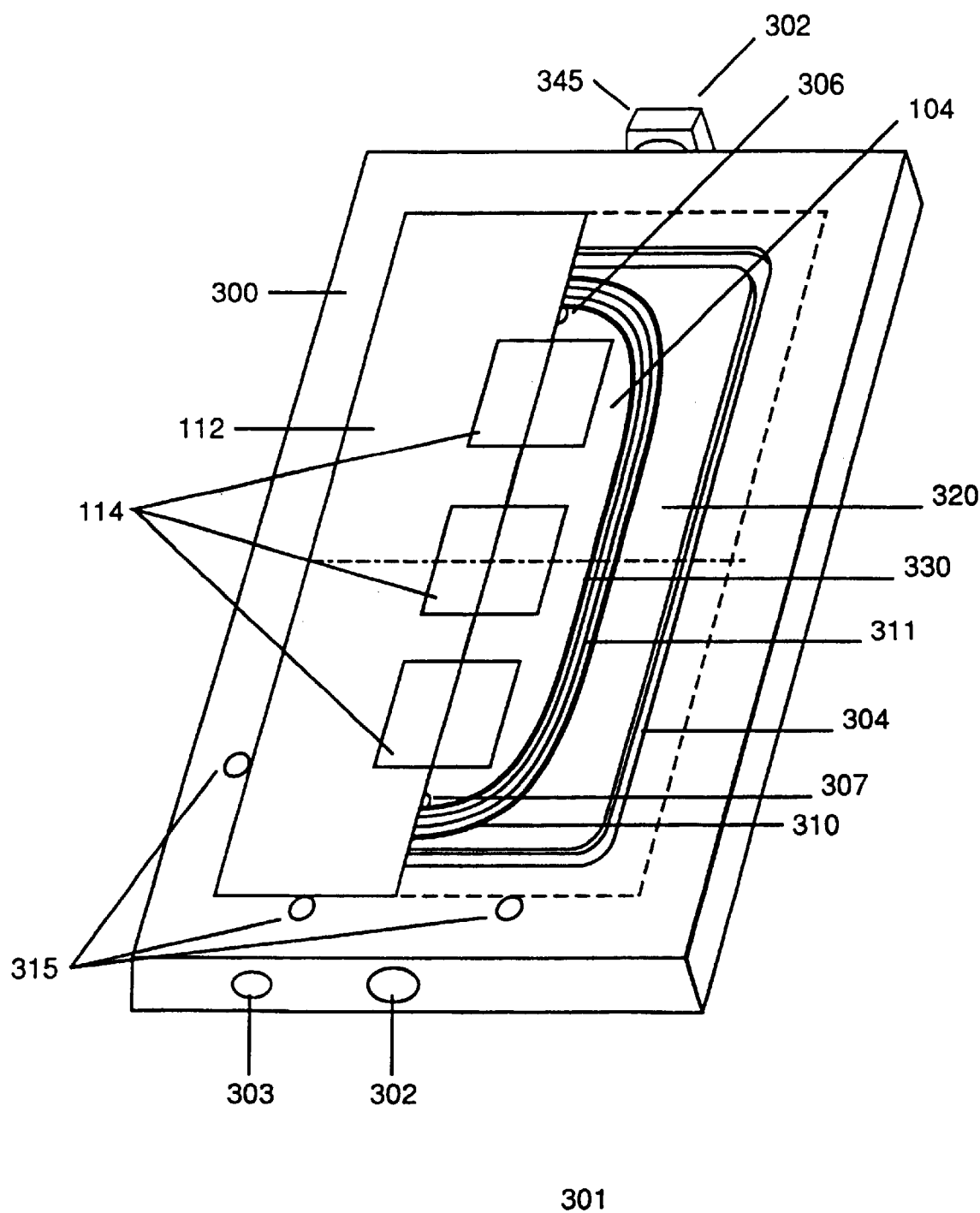
FIGS. 4A and 4B schematically illustrate different isolated views of a flow cell incorporated into the reactor systems of FIG. 3A and 3B.
Figure 4B:
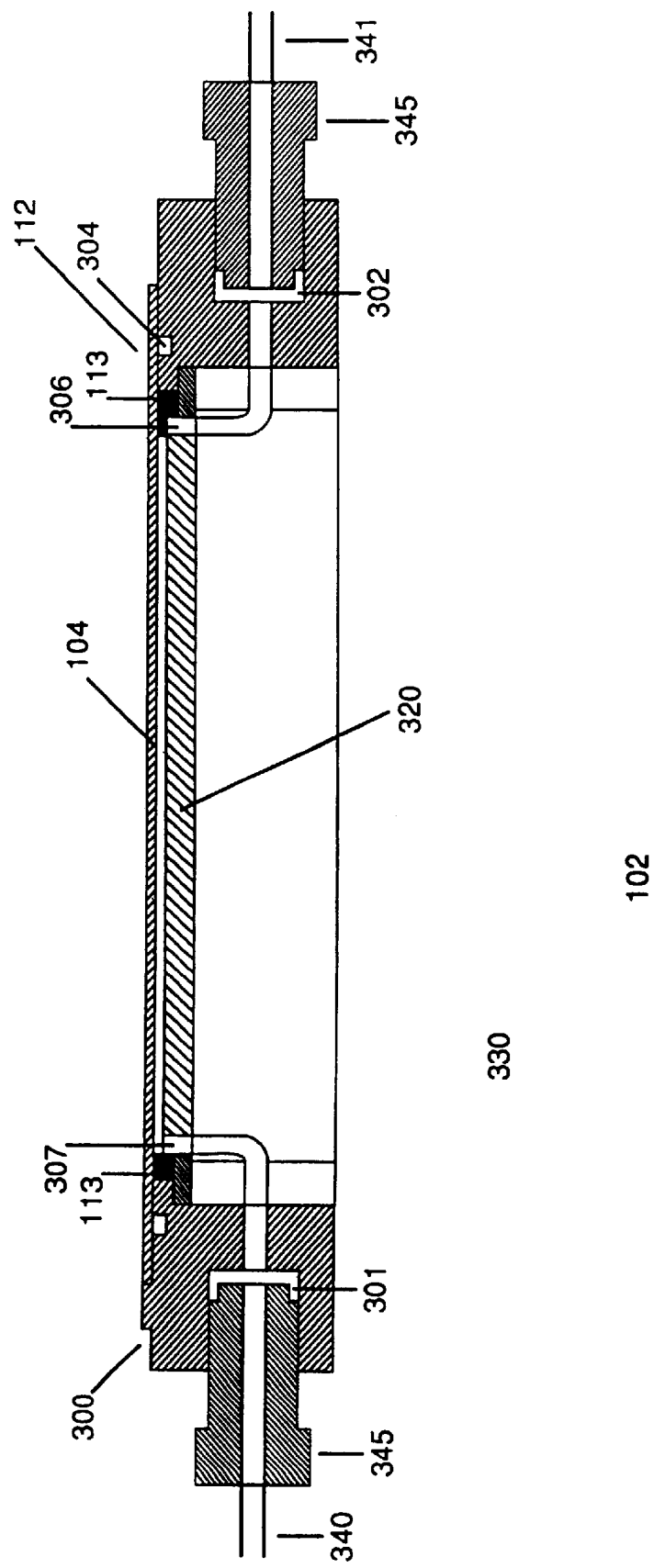

FIGS. 4A and 4B show different views of schematic illustrations of one embodiment of the flow cell portion of the device, e.g., the body substrate combination. As shown in FIGS. 4A and 4B, a panel 320 is mounted to the body 102 to form the bottom surface of the cavity 104. Silicone cement or other adhesive may be used to mount the panel and seal the bottom of the cavity. In particularly preferred aspects, panel 320 will be a light absorptive material, such as yellow glass, RG1000 nm long pass filter, or other material which absorbs light at the operating wavelengths, for eliminating or minimizing reflection of impinging light. As a result, the burden of filtering stray light at the incident wavelength during synthesis is significantly lessened. The glass panel also provides a durable surface for forming the cavity since it is relatively immune to corrosion in the high salt environments or other conditions common in DNA synthesis reactions or other chemical reactions.

The substrate wafer 112 is mated to a surface 300. The first surface 114 of wafer comprises the photolabile protecting groups coupled to functional groups coupled to the substrate surface, as described above. In some embodiments, vacuum pressure may be used to mate the wafer to the surface 300. In such embodiments, a groove 304, which may be about 2 mm deep and 2 mm wide, is formed on surface 300. The groove communicates with an opening 303 that is connected to a vacuum source, e.g., a pump. The vacuum source creates a vacuum in the groove and causes the substrate wafer to adhere to surface 300.

A groove 310 may be formed on surface 300 for seating a gasket 311 therein. The gasket ensures that the cavity is sealed when the wafer is mated to the flow cell. Alignment pins 315 may be optionally provided on surface 300 to properly align the substrate wafer on the flow cell.

Inlet port 307 and outlet port 306 are provided for introducing fluids into and flowing fluids out of the cavity. The flow cell provides an opening 301 in which a flow tube 340 is passed through for coupling to inlet port 307. Likewise, a flow tube 341 is passed through opening 302 for coupling with outlet port 306. Fittings 345 are employed to maintain the flow tubes in position. Openings 301 and 302 advantageously position the flow tubes so that the flow cell can easily and conveniently be mounted on the synthesis system.

A pump, which is connected to one of the flow tubes, circulates a selected fluid into the cavity and out through the outlet port for recirculation or disposal. The selected fluids may include, e.g., monomer containing solutions, index matching fluids, wash solutions or the like. Although described in terms of a pump, a variety of pressurized delivery systems may be used to deliver fluids to the cavity. Examples of these alternate systems utilize argon gas to circulate the selected fluid into and through the cavity. Simultaneously, the flow of argon gas may be regulated to create bubbles for agitating the fluid as it is circulated through the system. Agitation is used to mix the fluid contents in order to improve the uniformity and/or yield of the reactions.

As shown, inlet and outlet ports 306 and 307, respectively, are located at opposite ends of the panel. This configuration improves fluid circulation and regulation of bubble formation in the cavity. In one embodiment, the outlet and inlet are located at the top and bottom ends of the cavity, respectively, when the flow cell is mounted vertically on the synthesizer. Locating the outlet and inlet at the highest and lowest positions in the cavity, respectively, facilitates the removal of bubbles from the cavity.

In some embodiments, the flow cell may be configured with a temperature control system to permit the synthesis reactions to be conducted under optimal temperature conditions. Examples of temperature control systems include refrigerated or heated baths, refrigerated air circulating devices, resistance heaters, thermoelectric peltier devices and the like.

In some instances, it may be desirable to maintain the volume of the flow cell cavity as small as possible so as to more accurately control reaction parameters, such as temperature or concentration of chemicals. In addition to the benefits of improved control, smaller cavity volumes may reduce waste, as a smaller volume requires a smaller amount of material to carry out the reaction.

For particularly small cavity volumes, a difficulty may arise where bubbles in the reaction fluids can become trapped in the cavity, which may result in incomplete exposure of the substrate surface to the reaction fluid. In particular, when a fluid fills into a very shallow channel or slit, it will tend to fill the shallowest areas first, due to relatively strong capillary forces in those areas. If the channel is too shallow, inconsistency and non-flatness of the substrate which results in uneven capillary forces, will lead to an uneven fluid front during filling. As the liquid front loses its even shape, liquid may surround air or gas pockets to produce trapped bubbles. Accordingly, where particularly small cavity volumes are desired, a flow cell may be employed wherein the top and bottom surfaces of the flow cell are nonparallel, being narrower at the inlet of the flow cell, and growing wider toward the outlet. Uniform filling of the flow cell ensures that the fluid front maintains a straight shape, thereby minimizing the potential of having bubbles trapped between the surfaces.

Figure 4C:
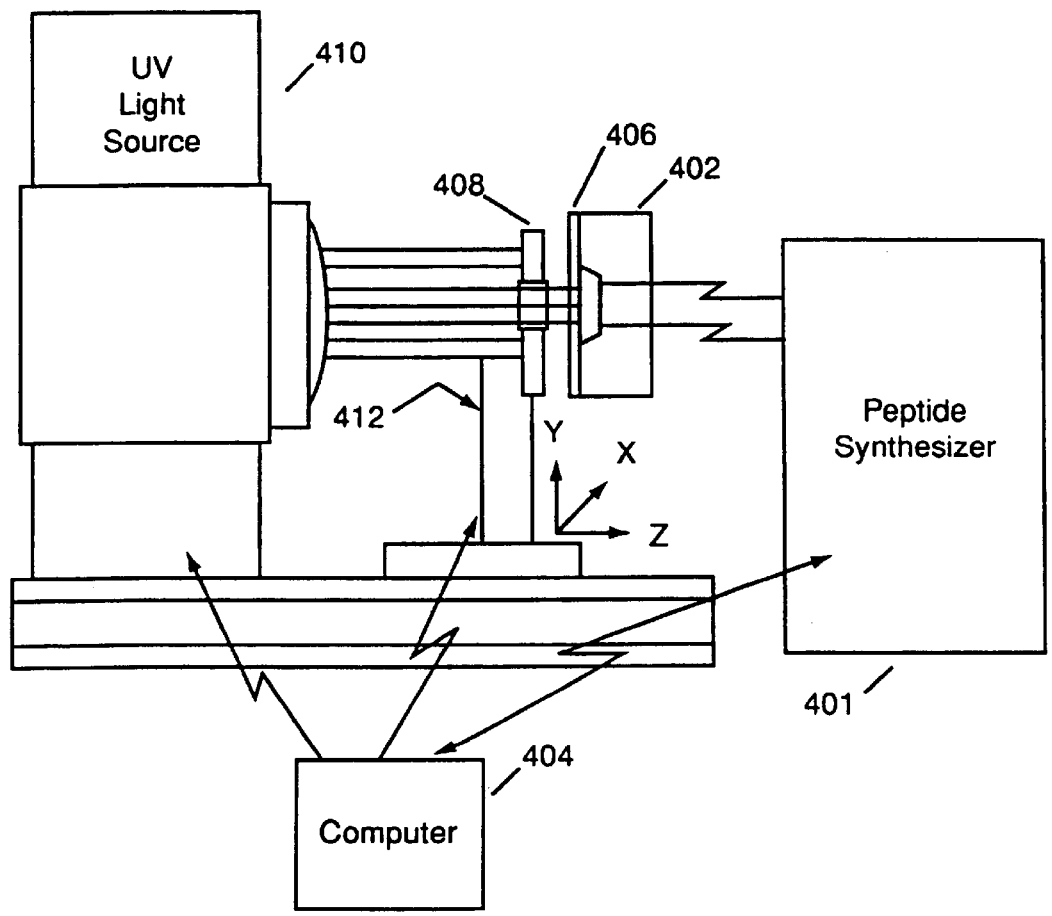
FIG. 4C shows a schematic illustration of an integrated reactor system including computer control and substrate translation elements.

A schematic illustration of one embodiment of an integrated reactor system is shown in FIG. 4C. The device includes an automated peptide synthesizer 401. The automated peptide synthesizer is a device which flows selected reagents through a flow cell 402 under the direction of a computer 404. In a preferred embodiment the synthesizer is an ABI Peptide Synthesizer, model no. 431A. The computer may be selected from a wide variety of computers or discrete logic including for, example, an IBM PC-AT or similar computer linked with appropriate internal control systems in the peptide synthesizer. The PC is provided with signals from the ABI computer indicative of, for example, the beginning of a photolysis cycle. One can also modify the synthesizer with a board that links the contacts of relays in the computer in parallel with the switches to the keyboard of the control panel of the synthesizer to eliminate some of the keystrokes that would otherwise be required to operate the synthesizer.

Substrate 406 is mounted on the flow cell, forming a cavity between the substrate and the flow cell. Selected reagents flow through this cavity from the peptide synthesizer at selected times, forming an array of peptides on the face of the substrate in the cavity. Mounted above the substrate, and preferably in contact with the substrate is a mask 408. Mask 408 is transparent in selected regions to a selected wavelength of light and is opaque in other regions to the selected wavelength of light. The mask is illuminated with a light source 410 such as a UV light source. In one specific embodiment the light source 410 is a model no. 82420 made by Oriel. The mask is held and translated by an x-y translation stage 412. Translation stages may be obtained commercially from, e.g., Newport Corp. The computer coordinates the action of the peptide synthesizer, translation stage, and light source. Of course, the invention may be used in some embodiments with translation of the substrate instead of the mask.

2. Photolysis step

As described above, photolithographic methods are used to activate selected regions on the surface of the substrate. Specifically, functional groups on the surface of the substrate or present on growing polymers on the surface of the substrate, are protected with photolabile protecting groups. Activation of selected regions of the substrate is carried out by exposing selected regions of the substrate surface to activation radiation, e.g., light within the effective wavelength range, as described previously. Selective exposure is typically carried out by shining a light source through a photolithographic mask. Alternate methods of exposing selected regions may also be used, e.g., fiberoptic faceplates, etc. For the individual process methods, e.g., the integrated photolysis/chemistry process, the substrate is mounted in the reactor system or flow cell such that the synthesis surface of the substrate is facing the cavity and away from the light source. As the light source is shown on the surface opposite that upon which the photoprotective groups are provided, this method of exposure is termed "back-side" photolysis.

Because the individual feature sizes on the surface of the substrate prepared according to the processes described herein can typically range as low as 1–10 $\mu$m on a side, the effects of reflected or refracted light at the surface of the substrate can have significant effects upon the ability to expose and activate features of this size. One method of reducing the occurrence of reflected light is to incorporate a light absorptive material as the back surface of the flow cell, as described above. Refraction of the light as it enters the flow cell, i.e., crosses the substrate/flow cell interface, through the back surface of the substrate can also result in a loss in feature resolution at the synthesis surface of the substrate resulting from refraction and reflection. To alleviate this problem, during the photolysis step, it is generally desirable to fill the flow cell with an index matching fluid ("IMF") to match the refractive index of the substrate, thereby reducing refraction of the incident light and the associated losses in feature resolution. The index matching fluid will typically have a refractive index that is close to that of the substrate. Typically, the refractive index of the IMF will be within about 10% that of the substrate, and preferably within about 5% of the refractive index of the substrate. Refraction of the light entering the flow cell, as it contacts the interface between the substrate and the IMF is thereby reduced. Where synthesis is being carried out on, e.g., a silica substrate, a particularly preferred IMF is dioxane which has a refractive index roughly equivalent to the silica substrate.

The light source used for photolysis is selected to provide a wavelength of light that is photolytic to the particular protecting groups used, but which will not damage the forming polymer sequences. Typically, a light source which produces light in the UV range of the spectrum will be used. For example, in oligonucleotide synthesis, the light source typically provides light having a wavelength above 340 nm, to effect photolysis of the photolabile protecting groups without damaging the forming oligonucleotides. This light source is generally provided by a Hg-Arc lamp employing a 340 nm cut-off filter (i.e., passing light having a wavelength greater than 340–350 nm). Typical photolysis exposures are carried out at from about 6 to about 10 times the exposed half-life of the protecting group used, with from 8–10 times the half-life being preferred. For example, MeNPOC, a preferred photolabile protecting group, has an exposed half-life of approximately 6 seconds, which translates to an exposure time of approximately 36 to 60 seconds.

Photolithographic masks used during the photolysis step typically include transparent regions and opaque regions, for exposing only selected portions of the substrate during a given photolysis step. Typically, the masks are fabricated from glass that has been coated with a light-reflective or absorptive material, e.g., a chrome layer. The light-reflective or absorptive layer is etched to provide the transparent regions of the mask. These transparent regions correspond to the regions to be exposed on the surface of the substrate when light is shown through the mask.

In general, it is desirable to produce arrays with smaller feature sizes, allowing the incorporation of larger amounts of information in a smaller substrate area, allowing interogation of larger samples, more definitive results from an interogation and greater possibility of miniaturization. Alternatively, by reducing feature size, one can obtain a larger number of arrays, each having a given number of features, from a single substrate wafer. The result is substantially higher product yields for a given process. This technique, generally referred to as "die shrinking" is commonly used in the semiconductor industry to enhance product outputs or to reduce chip sizes following a over-sized test run of a manufacturing process.

In seeking to reduce feature size, it is important to maximize the contrast between the regions of the substrate exposed to light during a given photolysis step, and those regions which remain dark or are not exposed. By "contrast" is meant the sharpness of the line separating an exposed region and an unexposed region. For example, the gradient of activated to nonactivated groups running from an activated or exposed region to a nonexposed region is a measure of the contrast. Where the gradient is steep, the contrast is high, while a gradual gradient indicates low or poor contrast.

One cause of reduced contrast is "bleed-over" from exposed regions to non-exposed regions during a particular photolysis step. In certain embodiments, contrast between features is enhanced through the front side exposure of the substrate. Front side exposure reduces effects of diffraction or divergence by allowing the mask to be placed closer to the synthesis surface. Additionally, and perhaps more importantly, refractive effects from the light passing through the substrate surface prior to exposure of the synthesis surface are also reduced or eliminated by front-side exposure. This is discussed in greater detail below.

Contrast between features may also be enhanced using a number of other methods. For example, the level of contrast degradation between two regions generally increases as a function of the number of differential exposures or photolysis steps between the two regions, i.e., incidences where one region is exposed while the other is not. The greater the number of these incidences, the greater the opportunity for bleed over from one region to the other during each step and the lower the level of contrast between the two regions regions. Translated into sequence information, it follows that greater numbers of differences between polymers synthesized in adjacent regions on a substrate can result in reduced contrast between the regions. Namely, the greater the number of differences in two polymer sequences, the greater the number of incidences of a region bearing the first polymer being exposed while the other was not. These effects are termed "edge" effects as they generally occur at the outer edges of the feature.

It is thus desirable to minimize these edge effects to enhance contrast in synthesis. Accordingly, in one aspect, the present invention provides a method of enhancing contrast by reducing the number of differential synthesis/photolysis steps between adjacent polymer sequence containing regions throughout an array.

One method of edge minimization is to divide the polymers to be sequenced into blocks of related polymers, leaving blank lanes between the blocks to prevent bleed-over into other blocks. While this method is effective in reducing edge effects, it requires the creation of a specific algorithm for each new tiling strategy. That is, the layout of each block in terms of probe location will depend upon the tiled sequence. In one aspect, the present invention provides methods for aligning polymer synthesis steps on an array whereby the number of differential.synthesis steps is reduced, and/or the syntheses in adjacent regions of the array are optimized for similarity.

The following example illustrates a typical synthesis strategy. Assuming a simple array where a single possible mutation is being explored at the third position in the sequence TGTATCA. An array of complementary probes might be as follows:

1 AC<u>A</u>TAGT
2 AC<u>T</u>TAGT
3 AC<u>G</u>TAGT
4 AC<u>C</u>TAGT where position 3 has been substituted with each of the four nucleotides. In synthesizing this array, monomer addition is typically cycled through the four nucleosides in a given preset order, e.g., 1-A, 2-C, 3-G, 4-T. Thus, for the array shown above, the first "A" in each of the sequences would be coupled in the first cycle. The second "C" would be coupled in the second monomer addition cycle. Each of the substituted positions would then be coupled in their respective cycle, e.g., the "A" in probe #1 would be coupled in the fifth cycle, while the "T", "G", and "C" would be coupled in the sixth, seventh, and eighth cycles, respectively.

Up to this point, each probe has been exposed to a minimal number of differential exposures, as described above. However, the monomer addition steps following the substituted monomer give rise to some difficulties in this regard. For example, it would be possible to couple the "T" in the fourth position in probe #1 at the sixth cycle while the "T" in the remaining probes would have to be added at the tenth cycle, because they could not be added before the preceding monomer in the sequence. The remaining synthesis steps for probe 1 would then be out of sequence with those of the remaining probes, resulting in an increased number of differential sequence steps between probe 1 and the remaining probes. By aligning the addition of the "T" monomer in probe #1 with that of the remaining probes, the number of differential synthesis steps is minimized. Specifically, by waiting until the tenth cycle to add the "T" in probe #1, the number of differential exposures between the probes is minimized to only that number necessary to incorporate the various mutations or substitutions.

The methods described herein utilize a generalized synthesis method for aligning synthesis steps to accomplish the above-described goal. These generalized methods can be followed regardless of the particular tiling strategy used or targeted sequence.

In particular, the methods described herein, identify each probe by a generic structure which is effectively independent of the actual targeted sequence. This generic description of a probe sequence is termed an "image", a collection of polymer sequences is termed a "picture", and a local translation, e.g., in a larger targeted sequence, is termed a "frame". The entire picture and frame structure is termed a "collage".

Each position in the probe is designated by the position number in the frame, or targeted sequence segment, followed by a number that indicates the rotation from the wild type monomer, with the wild type monomer being "0". By rotation is meant the number of cycles required to go from the wild type monomer to the substituted monomer in the addition cycle (note that a "0" and a "4" are the same monomer in terms of nucleotides). For example, if a given wild type sequence has an "A" in a given position, a substitution to a "G" would be identified by a rotation of "3", assuming a monomer addition or synthesis cycle of A, C, T, G.

In terms of the above example, probe #1, being the same as the wild type target as also described above, would be identified as:

1 <1,0><2,0><3,0><4,0><5,0><6,0><7,0> where each position is not rotated from the wild type, or is "unmodified." The remaining sequences would be identified as:

2 <1,0><2,0><3,1><4,0><5,0><6,0><7,0>
3 <1,0><2,0><3,2><4,0><5,0><6,0><7,0>
4 <1,0><2,0><3,3><4,0><5,0><6,0><7,0> indicating a rotation in the third position for each of the nucleoside monomers.

Sequence positions which are in the same layer are aligned to be added in the same synthesis cycle. The "depth" of the sequence or the"layer" in which a given monomer is found, are determined by counting each occurrence where an unmodified base follows a modified base. Each sequence has a depth of at least one. For example, the sequence "X" indicated by the <1,1><2,0><3,0> has a depth of 2, where <2,0> and <3,0> are in the second layer. Similarly, the sequence "Y" identified as <1,0><2,1><3,0> has a depth of two where <1,0> is in the first layer and <3,0> is in the second layer. Aligning these two sequences, it can be seen that the monomer <3,0> in sequences X and Y may be aligned as it exists in the same layer.

In contrast, the sequence "Z" <1,0><2,0><3,1> has a depth of one with <1,0><2,0> in the first layer. Thus, the position <2,0> in the sequence X would not be aligned with the same position in sequence Z as they exist in different layers.

A specific example of the collage method is illustrated using the following sequence/tiling strategy. A targeted sequence is complementary to the sequence CTTA. Thus, written in the above-described generic style, the wild type sequence would be designated <1,0><2,0><3,0><4,0>. Assuming a simplified tiling strategy where each position was to be substituted with a monomer rotated one from the wild type, the array would have the generic description:

| #1 | <1,1> | <2,0> | <3,0> | <4,0> |
|---|---|---|---|---|
| #2 | <1,0> | <2,1> | <3,0> | <4,0> |
| #3 | <1,0> | <2,0> | <3,1> | <4,0> |
| #4 | <1,0> | <2,0> | <3,0> | <4,1> | which would correspond to the sequences:

| #1 | G | T | T | A |
| #2 | C | A | T | A |
| #3 | C | T | A | A |
| #4 | C | T | T | C |

The assignment of bases of each layer to a particulr cycle is termed a "frame." For example, the frame for the above synthesis would be as follows:

| Layer 1 | Layer 2 |
|---|---|
| <1,0> = 2 | <---- |
| <2,0> = 8 | <2,0> = 8 |
| <3,0> = 12 | <3,0> = 12 |
|  | <4,0> = 13 |

Once monomers in the same layer are aligned, the synthesis is carried out with the following aligned cycle assignments:

```
Cy-
cleA  C  G  T  A  C  G  T  A  C  G  T  A  C  G  T
                         Layer 2
#1 _____ 3         8 _____ 12 13
#2  2 _____ 5                    12 13
#3  2    4  5                       13
#4  2    4        8    10
     Layer 1
```

The bases in the first layer are assigned the cycles closest to the start of the synthesis. The modified bases (between the layers) are assigned the next available cycles. The second layer is assigned a set of cycles as close as possible to the start of synthesis consistent with the bases already assigned (i.e., without altering the base ordering of any of the probes). Subsequent layers are assigned in a similar manner. This method allows maximum alignment of synthesis cycles throughout the frame being synthesized, while minimizing the total length of synthesis (e.g., number of steps).

Another method of minimizing bleed-over in the photolysis steps is to reduce the size of the transmissive or translucent portion of the mask, thus preventing unintentional exposure of adjoining regions caused by diffraction of the light shown through the mask. In particular, typical photolysis steps can have a duration of up to 8 to 10 times the half-life of the photodeprotection reaction. Thus, photoprotection can be up to 50% complete where the light intensity is only 12% of optimal levels, i.e., the level required for complete or near complete photodeprotection. Typically, such intensity levels may be reached well outside the feature boundary as defined by the transmissive portion of the mask.

Reducing the size of the transmissive portion of the mask allows diffraction, scattering and divergence at the edges of each feature without that diffraction interfering with neighboring features. Thus, the region of incomplete photolysis can be centered on the desired boundary between features. As a result, the total area of the chip that is compromised in a multi-step synthesis is minimized because bleed-over effects from each region are centered in the boundary rather than well into the neighboring feature. Accordingly, in one aspect of the present invention provides a method of minimizing bleed-over in adjoining cells by reducing the size of the transmissive portion of the mask, such that the zone of divergent light shown through the mask is centered on the desired feature border. As an example, a mask exposing a rectangular feature can be reduced by, e.g., 20 µm in each dimension, thus allowing greater homogeneity at the edges of 100 µm features. In preferred aspects, the translucent region of the mask will be from about 2% to about 25% smaller in each dimension of the size of the region which is to be exposed. In more preferred aspects, the translucent portion of the mask will be from about 10% to about 25% smaller in each dimension.

3. Chemistry Step

Following each photolysis step, a monomer building block is introduced or contacted with the synthesis surface of the substrate. Typically, the added monomer includes a single active functional group, for example, in the case of oligonucleotide synthesis, a 3'-hydroxyl group. The remaining functional group that is involved in linking the monomer within the polymer sequence, e.g., the 5'-hydroxyl group of a nucleotide, is generally photoprotected. The monomers then bind to the reactive moieties on the surface of the substrate, activated during the preceding photolysis step, or at the termini of linker molecules or polymers being synthesized on the substrate.

Typically, the chemistry step involves solid phase polymer synthesis methods that are well known in the art. For example, detailed descriptions of the procedures for solid phase synthesis of oligonucleotides by phosphoramidite, phosphite-triester, phosphotriester, and H-phosphonate chemistries are widely available. See, for example, Itakura, U.S. Pat. No. 4,401,796; Caruthers et al., U.S. Pat. Nos. 4,458,066 and 4,500,707; Beaucage et al., *Tetrahedron Lett.,* 22:1859–1862 (1981); Matteucci et al., *J. Amer. Chem. Soc.,* 103:3185–3191 (1981); Caruthers et al., *Genetic Engineering,* 4:1–17 (1982); Jones, chapter 2, Atkinson et al., chapter 3, and Sproat et al., chapter 4, in Gait, ed. *Oligonucleotide Synthesis: A Practical Approach,* IRL Press, Washington D.C. (1984); Froehler et al., *Tetrahedron Lett.,* 27:469–472 (1986); Froehler et al., *Nucleic Acids Res.,* 14:5399–5407 (1986); Sinha et al. *Tetrahedron Lett.,* 24:5843–5846 (1983); and Sinha et al., *Nucl. Acids Res.,* 12:4539–4557 (1984).

In operation, during the chemistry/monomer addition step, the IMF is removed from the flow cell through an outlet port. The flow cell is then rinsed, e.g., with water and/or acetonitrile. Following rinsing, a solution containing an appropriately protected monomer to be coupled in the particular synthesis step is added. For example, where the synthesis is of oligonucleotide probe arrays, being synthesized in the 3' to 5' direction, a solution containing a 3'-O-activated phosphoramidite nucleoside, photoprotected at the 5' hydroxyl is introduced into the flow cell for coupling to the photoactivated regions of the substrate. Typically, the phosphoramidite nucleoside is present in the monomer solution at a concentration of from 1 mM to about 100 mM, with 10 mM nucleoside concentrations being preferred. Typically, the coupling reaction takes from 30 seconds to 5 minutes and preferably takes about 1.5 minutes.

Following coupling, the monomer solution is removed from the flow cell, the substrate is again rinsed, and the IMF is reintroduced into the flow cell for another photolysis step. The photolysis and chemistry steps are repeated until the substrate has the desired arrays of polymers synthesized on its surface.

For each photolysis/chemistry cycle, it will generally be desirable to maximize coupling efficiencies in order to maximize probe densities on the arrays. Coupling efficiencies may be improved through a number of methods. For example, coupling efficiency may be increased by increasing the lipophilicity of the building blocks used in synthesis. Without being bound to any theory of operation, it is believed that such lipophilic building blocks have enhanced interaction at the surface of the preferred crystalline substrates. The lipophilicity of the building blocks may generally be enhanced using a number of strategies. In oligonucleotide synthesis, for example, the lipophilicity of the nucleic acid monomers may be increased in a number of ways. For example, one can increase the lipophilicity of the nucleoside itself, the phosphoramidite group, or the protecting group used in synthesis.

Figure 5A:
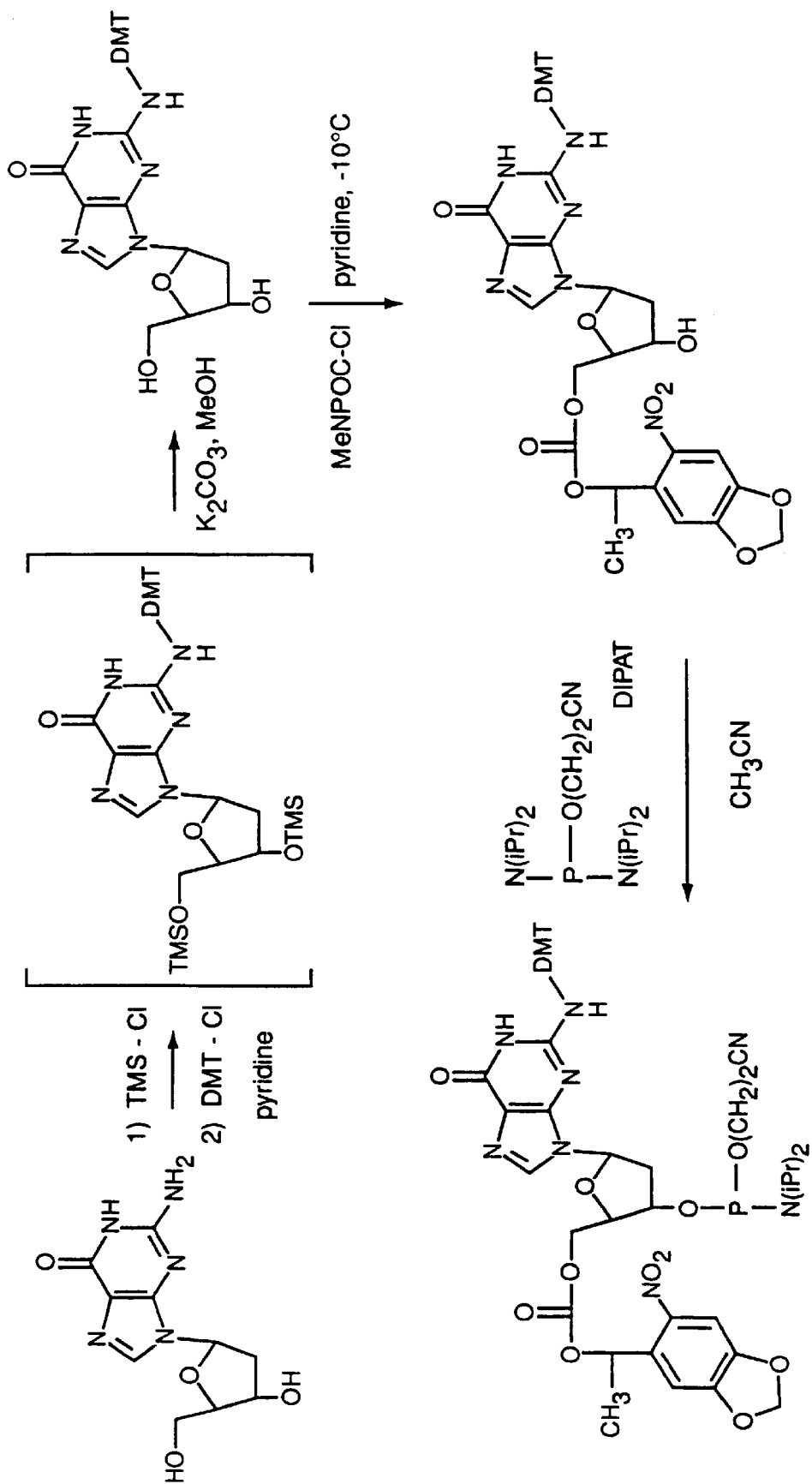
FIG. 5A shows the alkylation of the exocyclic amine functional group of deoxyguanosine with dimethoxytritylchloride (DMT-C1) and subsequent coupling of a MenPOC protecting group to the 3' hydroxyl group of a nucleoside phosphoramidite.

Modification of the nucleoside to increase its lipophilicity generally involves specific modification of the nucleobases. For example, deoxyguanosine (dG) may be alkylatea on the exocyclic amino group (N2) with DMT-Cl, after in situ protection of both hydroxyl groups as trimethylsilylethers (See, FIG. 5A). Liberation of the free DMT protected nucleoside is achieved by base catalyzed methanolosis of the di-TMS ether. Following standard procedures, two further steps are used resulting in the formation of 5'-MeNPOC-dG-phosphoramidites. The DMT group is used because the normally used 5'-DMT-phosphoramidites show high coupling efficiencies on silica substrate surfaces and because of the ease of synthesis for the overall compound. The use of acid labile protecting groups on the exocyclic amino groups of dG allows continued protection of the group throughout light-directed synthesis. Similar protection can be used for other nucleosides, e.g., deoxycytosine (dC). Protection strategies for nucleobase functional groups, including the exocyclic groups are discussed in U.S. patent application Ser. No. 08/445,332 filed May 19, 1995, previously incorporated herein by reference.

Figure 5B:
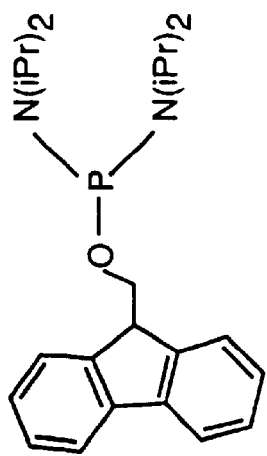
FIG. 5B shows the synthetic route for production of Fmoc-phosphoramidites.
Figure 5B:
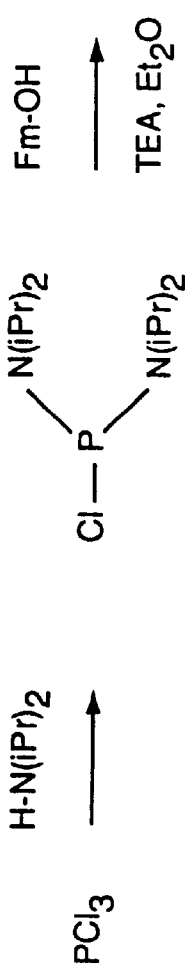

A more lipophilic phosphoramidite group may also be used to enhance synthesis efficiencies. Typical phosphoramidite synthesis utilizes a cyanoethyl-phosphoramidite. However, lipophilicity may be increased through the use of, e.g., an Fmoc-phosphoramidite group. Synthesis of Fmoc-phosphoramidites is shown in FIG. 5B. Typically, a phosphorus-trichloride is reacted with four equivalents of diisopropylamine, which leads to the formation of the corresponding monochloro-bisamino derivative. This compound reacts with the Fmoc-alcohol to generate the appropriate phosphatidylating agent.

Figure 5C:
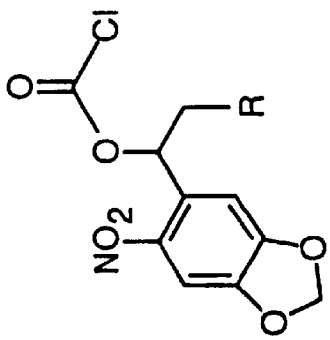
FIG. 5C shows a synthetic route for introduction of a lipophilic substituent to the photoprotecting group MeNPOC.
Figure 5C:
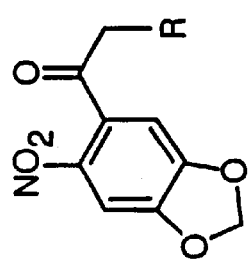
Figure 5C:
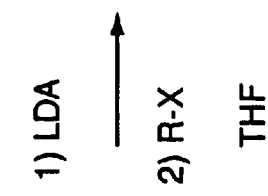
Figure 5C:
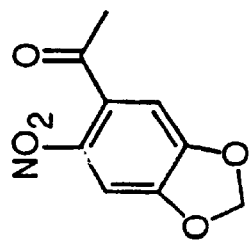

As with the phosphoramidite group, the photolabile protecting groups may also be made more lipophilic. For example, a lipophilic substituent, e.g., benzyl, naphthyl, and the like, may be introduced as an alkylhalide, through α-alkylation of a nitroketone, as shown in FIG. 5C. Following well known synthesis techniques, one generates the chloroformate needed to introduce the photoactive lipophilic group to the 5' position of a deoxyribonucleoside.

B. Batch Processing

In a second embodiment of the substrate preparation process, each of the photolysis and chemistry steps involved in the synthesis operation are provided as separate unit operations. This method provides advantages of efficiency and higher feature resolution over the single unit operation process. In particular, the separation of the photolysis and chemistry steps allows photolysis to be carried out outside of the confines of the flow cell. This permits application of the light directly to the synthesis surface, i.e., without first passing through the substrate. This "front-side" exposure allows for greater definition at the edges of the exposed regions (also termed "features") by eliminating the refractive influence of the substrate and allowing placement of the mask closer to the synthesis surface. A comparison illustrating the improved resolution of front-side synthesis is shown in FIGS. 8A–8D.

In addition to the benefits of front side exposure, the batch method provides advantages in the surface area of a substrate wafer that may be used in synthesizing arrays. In particular, by combining photolysis/chemistry aspects in the individual process methods, the operation of mounting the substrate wafer on the flow cell can result in less than the entire surface of the substrate wafer being used for synthesis. In particular, where the substrate wafer is used to form one wall of the flow cell, as is typically the case in these combined methods, engineering constraints involved in mounting of the flow cell can result in a reduction in the available substrate surface area. This is particularly the case where a vacuum chuck system is used to mount the substrate on the flow cell, where the vacuum chuck system requires a certain amount of surface area to hold the substrate on the flow cell with sufficient force.

In batch mode operation, the chemistry step is generally carried out by immersing the entire substrate wafer in the monomer solution, thus allowing synthesis over most if not all of the substrate wafer's synthesis surface. This results in a higher chip yield per substrate wafer than in the individual processing methods. Additionally, as the chemistry steps are generally the time limiting steps in the synthesis process, monomer addition by immersion permits monomer addition to multiple substrates at a given time, while more substrates are undergoing the photolysis steps.

For example, where synthesis is performed in the individual processing operation, as described above, the engineering constraints in vacuum mounting a substrate to a flow cell can result in a significant decrease in the size of a synthesis area on the substrate wafer. For example, in one process, a substrate wafer having dimensions of 5"×5" has only 2.5"×2.5" available as a synthesis surface, which when separated into chips of typical dimensions (e.g., 1.28 cm×1.28 cm) typically results in 16 potential chips per wafer. The same sized wafer, when subjected to the batch mode synthesis can have a synthesis area of about 4.3"×4.3", which can produce approximately 49 chips per wafer.

In general, a number of substrate wafers is subjected to the photolysis step. Following photolysis, the number of wafers is placed in a rack or "boat" for transport to the station which performs the chemistry steps, whereupon one or more chemistry steps are performed on the wafers, simultaneously. The wafers are then returned to the boat and transported back to the station for further photolysis. Typically, the boat is a rack that is capable of carrying several wafers at a time and is also compatible with automated systems, e.g., robotics, so that the wafers may be loaded into the boat, transported and placed into the chemistry station, and following monomer addition returned to the boat and the photolysis station, all through the use of automated systems.

Initial substrate preparation is the same for batch processing as described in the individual processing methods, above. However, beyond this initial substrate preparation, the two process take divergent paths. In batch mode processing, the photolysis and chemistry steps are performed separately. As is described in greater detail below, the photolysis step is generally performed outside of the flow cell. This can cause some difficulties, as there is no provision of an IMF behind the substrate to prevent the potentially deleterious effects of refraction and reflection of the photolytic light source. In some embodiments, however, the same goal is accomplished by applying a coating layer to the back-side of the substrate, i.e., to the non-synthesis surface of the substrate. The coating layer is typically applied after the substrate preparation process, but prior to derivatization. This coating is typically selected to perform one or more of the following functions: (1) match the refractive index of the substrate to prevent refraction of light passing through the substrate which may interfere with the photolysis; and (2) absorb light at the wavelength of light used during photolysis, to prevent back reflection which may also interfere with photolysis.

Typically, suitable coating materials may be selected from a number of suitable materials which have a refractive index approximately equal to that of the substrate and/or absorb light at the appropriate wavelength. In particular, index matching coatings are typically selected to have a refractive index that is within at about 10% that of the substrate, and preferably within about 5%. similarly, light absorbing coatings are typically selected whereby light at the photolytic wavelength is absorbed, which in preferred aspects is light in the ultraviolet range, e.g., between 280 nm and 400 nm. Light absorbing coatings and index matching coatings may be combined to provide combined protection against refraction and reflection, or a single coating material may be selected which possesses both of the desired properties.

Preferred polymers will typically be selected to be compatible with the various reaction conditions which would be encountered during the synthesis process, e.g., insoluble in and non-reactive with synthesis reagents, and resistant to the mechanical forces involved in handling and manipulating the substrate, throughout the synthesis process. Additionally, preferred coating materials are easily removable upon completion of the synthesis process, e.g., in the final deprotection step or in a final coating removal step.

Examples of suitable coating materials include anti-reflective coatings that are well known in the art and generally commercially available, e.g., magnesium fluoride compounds, which are light-absorbing in the desired wavelength range, polymethylmethacrylate coatings (PMMA), which have a refractive index comparable to glass substrates, and polyimide coatings which are both light-absorbing in the desired wavelength range, and have a refractive index close to that of a glass substrate. Polyimide coatings are most preferred.

Application of the coating materials may be carried out by a variety of methods, including, e.g., vapor deposition, spray application, and the like. In preferred aspects, the coating solution will be applied to the substrate using a spin-coating method. Typically, this involves spinning the substrate during deposition of the coating solution on the substrate surface that is to be coated. The spinning substrate results in spreading of the coating solution radially outward on the surface of the substrate.

Application of the coating material using the spin-coating process usually employs a two-speed spinning of the substrate. The application of the coating material to the surface of the substrate and initial spreading of the coating solution are usually carried out at low rotational speeds and for relatively short duration. For example, to apply 1 ml of a 12% solids w/v polymer coating solution to a 4.3"×4.3" substrate, initial spreading is carried out at 500 r.p.m. for 10 seconds. Elimination of excess polymer solution and evening of the polymer layer are carried out at higher rotational speeds and for substantially longer durations. For example in the application described above, the second spinning step is carried out at approximately 3000 r.p.m. for 30 seconds. It will be understood by those of skill in the art, that the above described parameters for spin-coating can be varied within the scope of the present invention. For example, where higher concentration (w/v) polymer solutions are used, it may be desirable to increase one or both rotational speeds, as well as the time at a given speed. Similarly, where the polymer concentration in the polymer solution is reduced, lower speeds and shorter spin times may be used.

Following application, the polymer coating is then cured on the surface of the substrate. Curing is typically carried out by heating the coated substrate. In preferred processes, the curing process involves a two-step heating process. The first step involves a "soft-bake" heating of the coated substrate to initially cure the polymer coating. This soft-bake step typically takes place at relatively low temperatures for relatively short periods, i.e., 85° C. for 5 minutes. The second step of the curing process is a final curing of the polymer coating which is typically carried out at higher temperatures for longer periods, i.e., 220–360° C., for approximately 60 minutes. In preferred aspects, a polymer coating applied to the back side of the substrate will be from about 1 to about 50 $\mu$m thick, and more preferably, from about 5 to about 20 $\mu$m thick, with polymer coating of about 10 $\mu$m thick being most preferred.

The back-side coated substrate is then subjected to derivitization, rinsing and baking, according to the above described methods.

As described previously, the steps of photolysis and monomer addition in the batch mode aspects of the present invention are performed in separate unit operations. Separation of photolysis and chemistry steps allows a more simplified design for a photolyzing apparatus. Specifically, the apparatus need not employ a flow cell. Additionally, the apparatus does not need to employ a particular orientation to allow better filling of the.flow cell. Accordingly, the apparatus will typically incorporate one or more mounting frames to immobilize the substrate and mask during photolysis, as well as a light source. The device may also include focusing optics, mirrors and the like for directing the light source through the mask and at the synthesis surface of the substrate. As described above, the substrate is also placed in the device such that the light from the light source impacts the synthesis surface of the substrate before passing through the substrate. As noted above, this is termed "front-side" exposure.

Typically a photolysis step requires far less time than a typical chemistry step, e.g., 60 seconds as compared to 10 minutes. Thus, in the individual processing mode where the photolysis and chemistry steps are combined, the photolysis machinery sits idle for long periods of time during the chemistry step. Batch mode operation, on the other hand, allows numerous substrates to be photolyzed while others are undergoing a particular chemistry step. For example, a number of substrate wafers may be exposed for a given photolysis step. Following photolysis, the several substrate wafers may be transferred to a number of reaction chambers for the monomer addition step. While monomer addition is being carried out, additional substrate wafers may be undergoing photolysis.

Figure 6A:
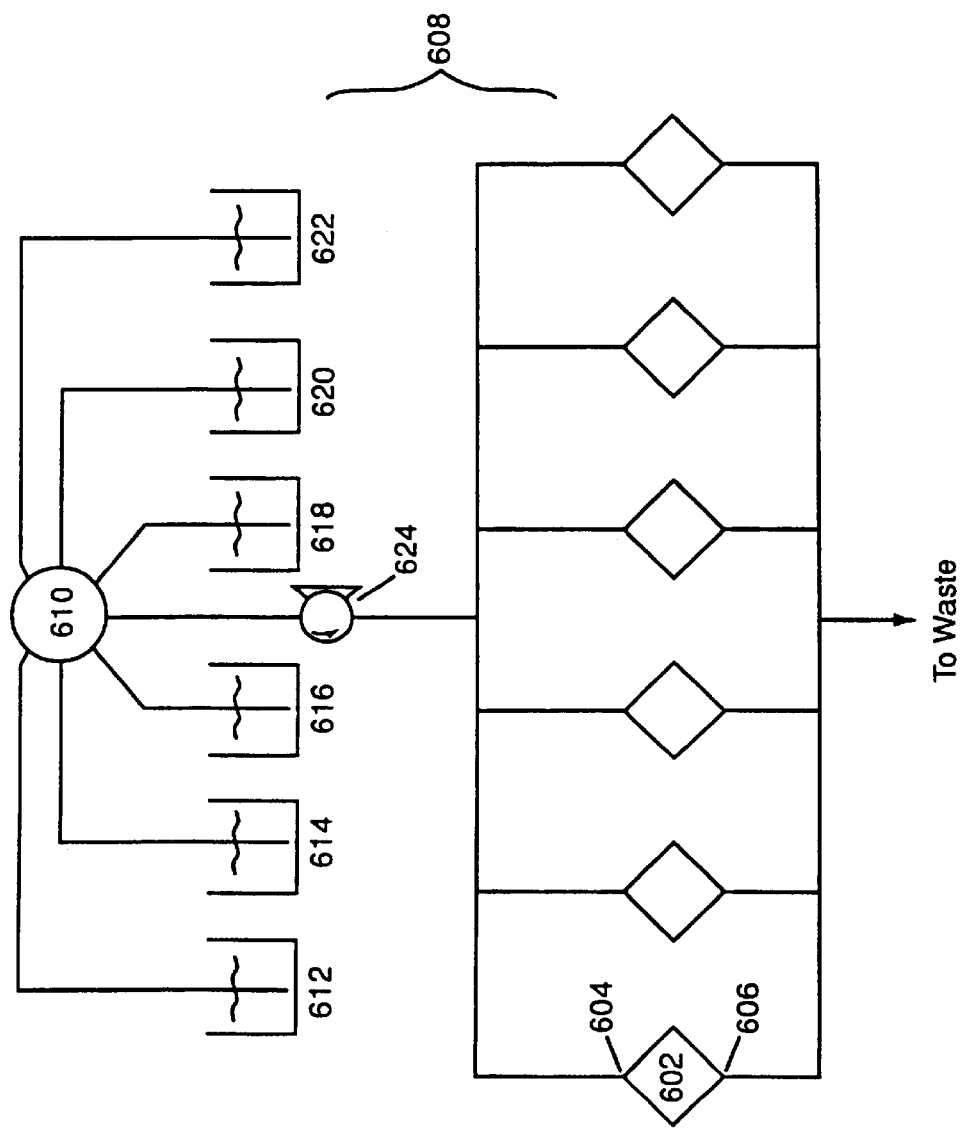
FIG. 6A shows a schematic representation of a device including a six vessel reaction chamber bank, for carrying out multiple parallel monomer addition steps separate from the photolysis step in light directed synthesis of oligonucleotide arrays.

FIG. 6A schematically illustrates a bank of reaction chambers for carrying simultaneous monomer addition steps on a number of separate substrates in parallel. As shown, the bank of reaction chambers is configured to simultaneously perform identical synthesis steps in each of the several reaction chambers. Each reaction chamber 602 is equipped with a fluid inlet 604 and outlet 606 for flowing various fluids into and through the reaction chamber. The fluid inlet of each chamber is generally fluidly connected to a manifold

608 which connects all of the reaction chambers, in parallel, to a single valve assembly 610. Typically, rotator valves are preferred for this aspect of the apparatus. The valve assembly allows the manifold to be fluidly connected to one of a plurality of reagent vessels 612–622. Also included is a pump 624 for delivering the various reagents to the reaction chamber. Although primarily described as performing the same synthesis steps in parallel, the bank of reaction chambers could also be readily modified to carry out to perform multiple independent chemistry steps. The outlet ports 606 from the reaction chambers 602 are typically fluidly connected to a waste vessel (not shown).

Figure 6B:
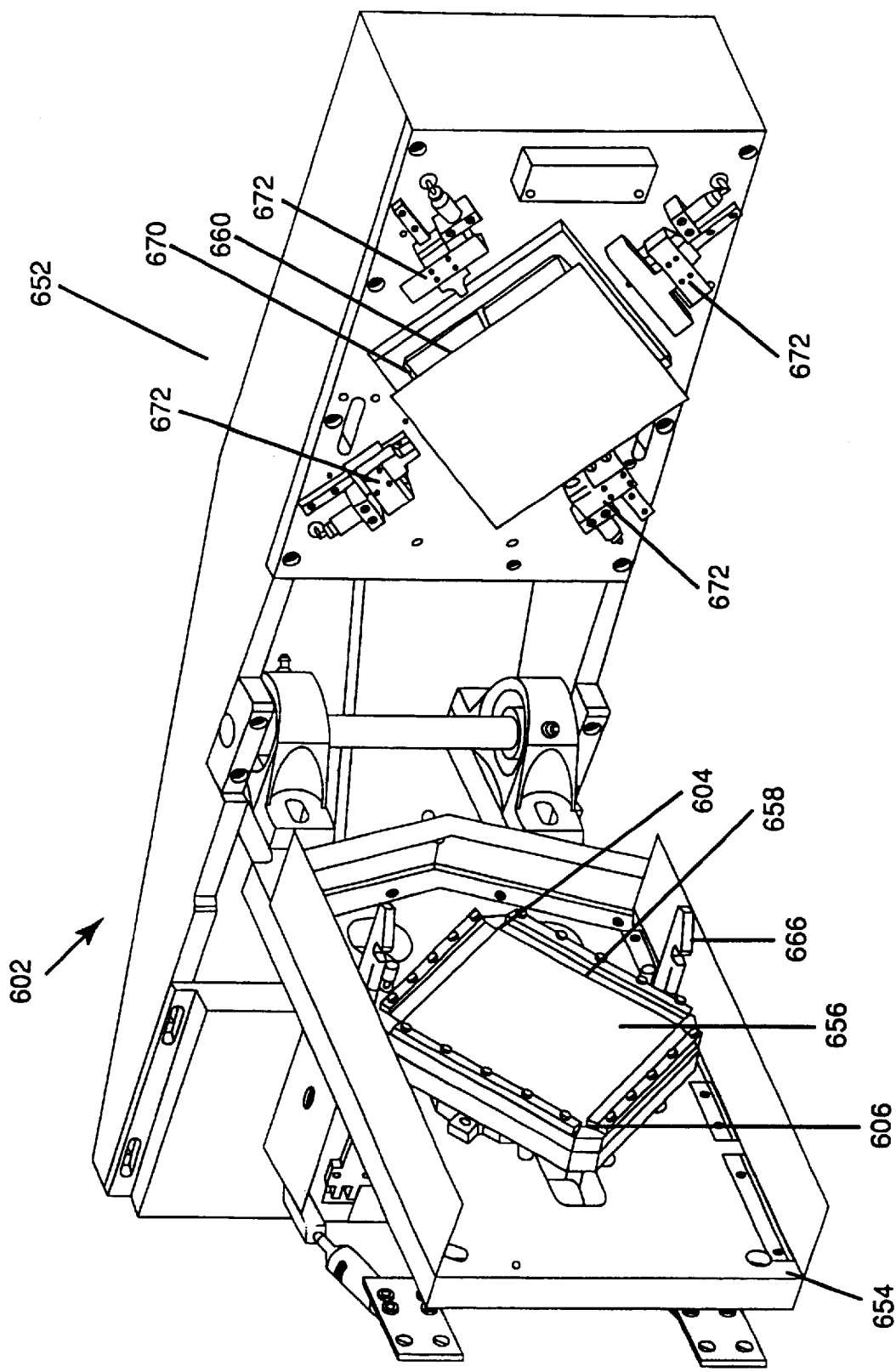
FIG. 6B shows a detailed view of a single reaction chamber.

FIG. 6B shows a schematic representation of a single reaction chamber for performing the chemistry steps of the batch process, e.g., monomer addition. As shown, the reaction chamber employs a "clam-shell" design wherein the substrate is enclosed in the reaction chamber 602 when the door 652 is closed against the body 654 of the apparatus. More particularly, the substrate wafer 660 is mounted on the chamber door and held in place, e.g., by a vacuum chuck shown as vacuum groove 670. When the door 652 is closed, the substrate wafer 668 is placed into the reactor cavity 656 on the body of the device. The reactor cavity is surrounded by a gasket 658, which provides the seal for the reaction chamber when the door is closed. Upon closing the door, the substrate wafer is pressed against the gasket and the pressure of this contact seals the reaction chamber. The reaction chamber includes a fluid inlet 604 and a fluid outlet 606, for flowing monomer solutions into and out of the reaction chamber.

The apparatus may also include latches 666, for locking the reaction chamber in a sealed state. Once sealed, reagents are delivered into the reaction chamber through fluid inlet 662 and out of the reaction chamber through fluid outlet 664. The reaction chamber also typically includes a temperature control element for maintaining the reaction chamber at the optimal synthesis temperature. As shown, the reaction chamber includes automatic alignment pins 672, e.g., solenoid or servo operated, for aligning a substrate wafer on the vacuum groove 670.

Following a monomer addition step, the substrate wafers are each subjected to a further photolysis step. The process may generally be timed whereby during a particular chemistry step, a new series of wafers is being subjected to a photolysis step. This dramatically increases the throughput of the process.

Following overall synthesis of the desired polymers on the substrate wafers, permanent protecting groups, e.g., those which were not removed during each synthesis step, typically remain on nucleobases and the phosphate backbone of synthetic oligonucleotides. Removal of these protecting groups is usually accomplished with a concentrated solution of aqueous ammonium hydroxide. While this method is effective for the removal of the protecting groups, these conditions can also cleave the synthetic oligomers fiom the support (usually porous silica particles) by hydrolyzing an ester linkage between the oligo and a functionalized silane derivative that is bonded to the support. In VLSIPS oligonucleotide arrays, it is desirable to preserve the linkage connecting the oligonucleotides to the glass after the final deprotection step. For this reason, synthesis is carried out directly on glass which is derivatized with a hydroxyalkyl-trialkoxysilane (e.g., bis(hydroxyethyl) aminopropylsilane). However, these supports are not completely stable to the alkaline hydrolysis conditions used for deprotection. Depending upon the duration, substrates left in aqueous ammonia for protracted periods can suffer a loss of probes due to hydroxide ion attack on the silane bonded phase.

Accordingly, in preferred embodiments, final deprotection of the polymer sequences is carried out using anhydrous organic amines. In particular, primary and secondary alkylamines are used to effect final deprotection. The alkylamines may be used undiluted or in a solution of an organic solvent, e.g. ethanol, acetonitrile, or the like. Typically, the solution of alkyl amine will be at least about 50% alkylamine (v/v). A variety of primary and secondary amines are suitable for use in deprotection, including ammonia, simple low molecular weight ($C_{1-4}$)alkylamines, and substituted alkylamines, such as ethanolamine and ethylenediamine. More volatile amines are preferred where removal of the deprotection agent is to be carried out by evaporation, whereas the less volatile amines are preferred in instances where it is desirable to maintain containment of the deprotection agent and where the solutions are to be used in repeated deprotections. Solutions of ethanolamine or ethylenediamine in ethanol have been used in deprotecting synthetic oligonucleotides in solution. See, Barnett, et al., Tet. Lett. (1981) 22:991–994, Polushin, et al, (1991) N.A.R. Symp. Ser. No. 24:49–50 and Hogrefe, et al. N.A.R. (1993) 21:2031–2038.

Depending upon the protecting groups to be removed, the time required for complete deprotection in these solutions ranges from several minutes for "fast" base-protecting groups, e.g. PAC or DMF-protected A, C or G and Ibu-protected C, to several hours for the standard protecting groups , e.g. benzoyl-protected A, C or G and Ibu-protected G,. By comparison, even the fast protecting groups require 4–8 hours for complete removal in aqueous ammonia. During this time, a significant percentage (e.g., 20–80%) of probes are cleaved from a glass substrate through hydrolytic cleavage of the silane layer, whereas after 48 hours of exposure to 50% ethanolic ethylenediamine solution, 95% of the probes remain on the substrate.

VI. Assembly of Probe Array Cartridges

Following synthesis, final deprotection and other finishing steps, e.g. polymer coat removal where necessary, the substrate wafer is assembled for use as individual substrate segments. Assembly typically employs the steps of separating the substrate wafer into individual substrate segments, and inserting or attaching these individual segments to a housing which includes a reaction chamber in fluid communication with the front surface of the substrate segment, e.g., the surface having the polymers synthesized thereon.

Methods of separating and packaging substrate wafers are described in substantial detail in Published PCT Application No. 95/33846, which is hereby incorporated herein by reference in its entirety for all purposes.

Figure 7:
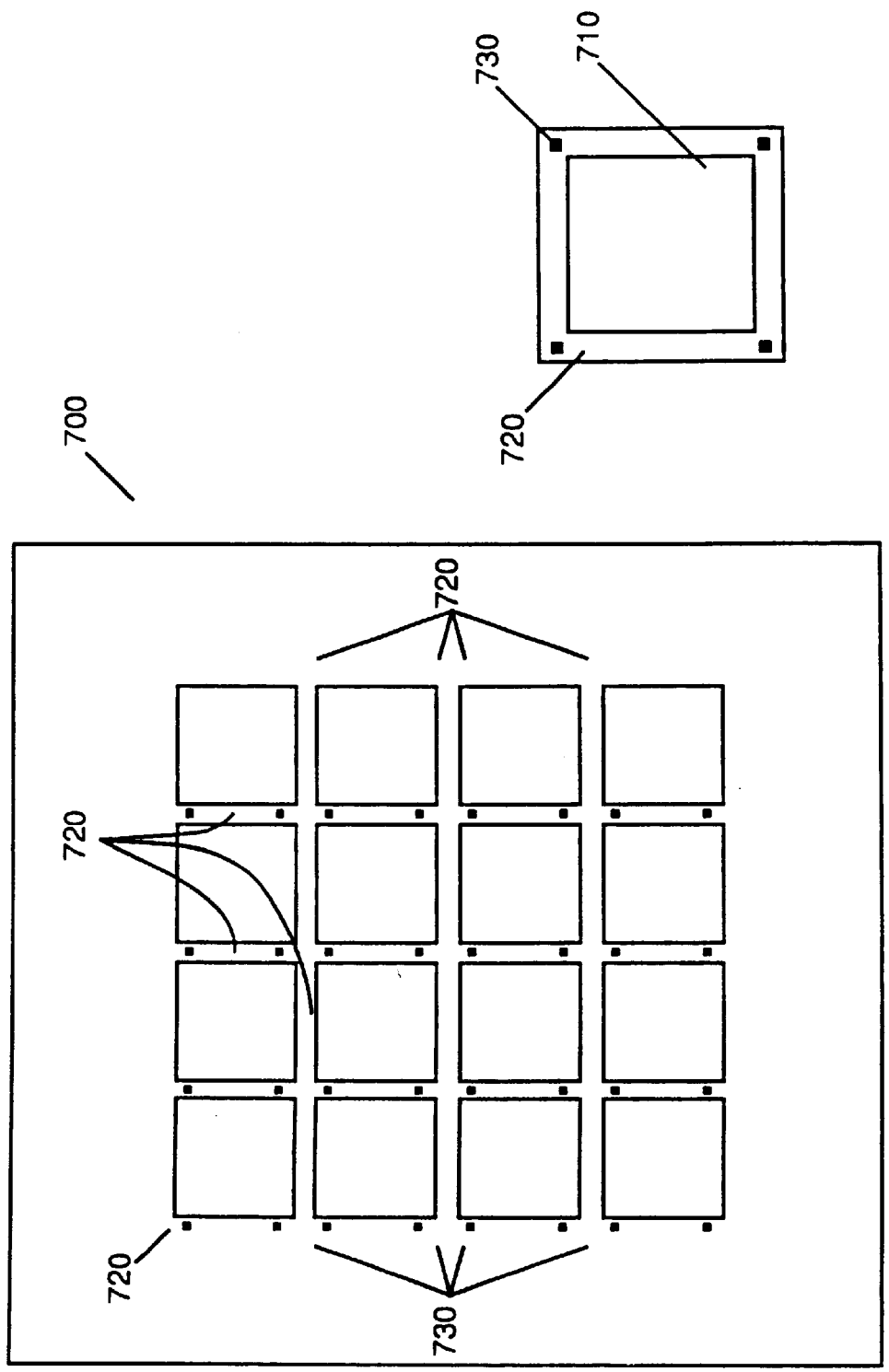
FIG. 7 illustrates a substrate wafer fabricated with a plurality of probe arrays which wafer also includes alignment marks.

Typically, the arrays are synthesized on the substrate wafer in a grid pattern, with each array being separated from each other array by a blank region where no compounds have been synthesized. These separating regions are termed "streets". The wafer typically includes a number of alignment marks located in these streets. These marks serve a number of purposes, including aligning the masks during synthesis of the arrays as described above, separation of the wafer into individual chips and placement of each chip into its respective housing for subsequent use, which are both described in greater detail below. An illustration of a wafer including these alignment marks is shown in FIG. 7. As shown, substrate wafer 700 includes individual arrays 710 separated by streets 720 and includes alignment marks 730.

Generally, the substrate wafer can be separated into a number of individual substrates using scribe and break methods that are well known in the semiconductor manufacturing industry. For example, well known scribe and break devices may be used for carrying out the separation steps, e.g., a fully programmable computer controlled scribe and break devices, such as a DX-III Scriber-Breaker manufactured by Dynatex International™, or the LCD-1 scriber/dicer manufactured by Loomis Industries. The steps typically involve scribing along the desired separation points, e.g., between the individual synthesized arrays on the substrate wafer surface, followed by application of a breaking force along the scribe line. For example, typical scribe and break devices break the wafer by striking the bottom surface of the wafer along the scribe lines with an impulse bar, or utilizing a three point beam substrate bending operation. The shock from the impulse bar fractures the wafer along the scribe line. Because the majority of force applied by the impulse bar is dissipated along the scribe line, the device is able to provide high breaking forces without exerting significant force on the substrate itself, allowing separation of the wafer without damaging the individual chips.

In alternative methods, the wafer may be separated into individual segments by, e.g., sawing methods, such as those described in U.S. Pat. No. 4,016,855.

Once the wafer is separated into individual segments, these segments may be assembled in a housing that is suited for the particular analysis for which the array will be used. Examples of methods and devices for assembling the substrate segments or arrays in cartridges are described in, e.g., U.S. patent application Ser. No. 08/485,452, previously incorporated by reference. Typically, the housing includes a body having a cavity disposed within it. The substrate segment is mounted over the cavity on the body such that the front side of the segment, e.g., the side upon which the polymers have been synthesized, is in fluid communication with the cavity. The bottom of the cavity may optionally include a light absorptive material, such as a glass filter or carbon dye, to prevent impinging light from being scattered or reflected during imaging by detection systems. This feature improves the signal-to-noise ratio of such systems by significantly reducing the potential imaging of undesired reflected light.

The cartridge also typically includes fluid inlets and fluid outlets for flowing fluids into and through the cavity. A septum, plug, or other seal may be employed across the inlets and/or outlets to seal the fluids in the cavity. The cartridge also typically includes alignment structures, e.g., alignment pins, bores, and/or an asymmetrical shape to ensure correct insertion and/or alignment of the cartridge in the assembly devices, hybridization stations, and reader devices.

Figure 8:
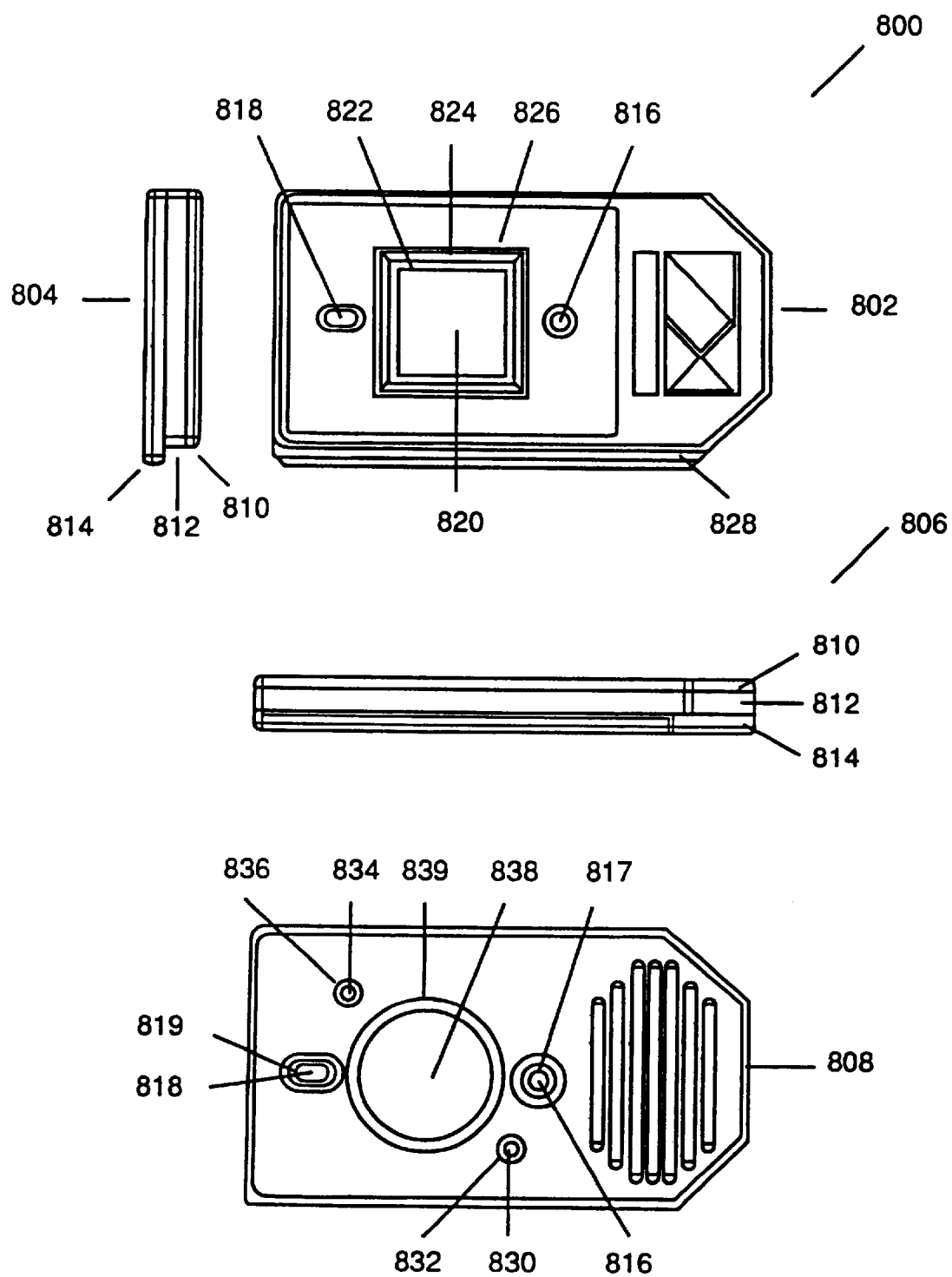
FIG. 8 illustrates one embodiment of an array cartridge into which an array substrate is placed for use.

An illustration of one embodiment of the array cartridge is shown in FIG. 8. FIG. 8 shows a top view 802, end view 804, side view 806 and bottom view 808 of the array cartridge 800. The body of the array cartridge may generally be fabricated from one or more parts or casings 810–814 that are made using a number of manufacturing techniques. In preferred aspects, the cartridge is fabricated from two or more injection molded plastic parts. Injection molding enables the parts to be formed inexpensively. Also, assembling the cartridge from two parts simplifies the construction of various features, such as the internal channels for introducing fluids into the cavity. As a result, the cartridges may be manufactured at a relatively low cost.

The top and bottom views of the cartridge include alignment structures, such as alignment holes 816 and 818. As shown, these alignment holes are disposed through the body of the cartridge, however, those of ordinary skill will appreciate that other alignment structures, e.g., alignment pins, etc., would be equally useful. As shown in the bottom view 808, alignment holes 816 and 818 also include an annular bevelled region to assist in insertion of complementary alignment pins on the hybridization station.

Referring to the top view 802 of the cartridge 800, cavity 820 includes a flat bottom peripheral portion 822, a bevelled portion 824 extending from the flat bottom peripheral portion, and a flat upper portion 826 surrounding the bevelled portion. The array includes an outer periphery which rests against the flat bottom peripheral portion 822. The bevelled portion aligns the chip onto the flat bottom peripheral portion 822. As shown, the top casing 814 extends outside the middle and bottom casings, 812 and 810, respectively, to provide a nonflush edge 828. The alignment structures 816 and 818, as well as the non flush edge 828, ensure proper orientation of the cartridge in the hybridization station, as well as other devices used in producing and reading polymer arrays. Surrounding mounting structures 816 and 818 are annular recesses 817 and 819, respectively, which aid in guiding the cartridge onto complementary mounting structures on the various devices.

As shown in the bottom view 808, the cartridge includes inlet and outlet ports 830 and 834, which include a bevelled annular region 832 and 836 surrounding these ports, respectively, to assist with fluid flow therethrough. Typically, the inlet and outlet ports will include septa disposed across the ports (not shown). Bottom casing 810 also includes a cavity 838, located adjacent the array, which cavity may be adapted for receiving a temperature monitoring and/or controlling device. As shown the cavity 838 has an annular recessed region 839 surrounding it, to ensure that the temperature controller may be inserted with maximum ease.

The array cavity 820 is preferably located at a center of the bottom casing, but may also be at other locations. The cavity may be round, square, rectangular, or any other shape, and orientation. The cavity is preferably smaller than the surface area of the chip to be placed thereon, and has a volume sufficient to perform hybridization and the like. In one embodiment, the cavity includes dimensions such as a length of about 0.6 inch, a width of about 0.6 inch and a depth of about 0.07 inch.

In a preferred embodiment, the bottom casing with selected cavity dimensions may be removed from the middle and top casings, and replaced with another bottom casing with different cavity dimensions. This allows a user to attach a chip having a different size or shape by changing the bottom casing, thereby providing ease in using different chip sizes, shapes, and the like. Of course, the size, shape, and orientation of the cavity will depend upon the particular application. The body of the cartridge may generally be fabricated from one or more parts made using a number of manufacturing techniques. In preferred aspects, the cartridge is fabricated from two or more injection molded plastic parts. Injection molding enables the casings to be formed inexpensively. Also, assembling the cartridge from two parts simplifies the construction of various features, such as the internal channels for introducing fluids into the cavity. As a result, the cartridges may be manufactured at a relatively low cost.

The substrate segment may be attached to the body of the cartridge using a variety of methods. In preferred aspects, the substrate is attached using an adhesive. Preferred adhesives are resistant to degradation under conditions to which the cartridge will be subjected. In particularly preferred aspects, an ultraviolet cured adhesive attaches the substrate segment to the cartridge. Devices and methods for attaching the substrate segment are described in Published PCT Application No. 95/33846, previously incorporated by reference. Particularly preferred adhesives are commercially available from a variety of commercial sources, including Loctite Corp. and Dymax Corp.

A variety of modifications can be incorporated in the assembly methods and devices that are generally described herein, and these too are outlined in greater detail in published PCT Application No. 95/33846.

Upon completion, the cartridged substrate will have a variety of uses. For example, the cartridge can be used in a variety of sequencing by hybridization ("SBH") methods, sequence checking methods, diagnostic methods and the like. Arrays which are particularly suited for sequence checking and SBH methods are described in, e.g. U.S. patent application Ser. Nos. 08/505,919, filed Jul. 24, 1995, 08/441, 887, filed May 16, 1995, 07/972,007, filed Nov. 5, 1992, each of which is incorporated herein by reference in its entirety for all purposes.

Typically, in carrying out these methods, the cartridged substrate is mounted on a hybridization station where it is connected to a fluid delivery system. The fluid delivery system is connected to the cartridge by inserting needles into the inlet and outlet ports through the septa disposed therein. In this manner, various fluids are introduced into the cavity for contacting the probes synthesized on the front side of the substrate segment, during the hybridization process.

Usually, hybridization is performed by first exposing the sample with a prehybridization solution. Next, the sample is incubated under binding conditions for a suitable binding period with a sample solution that is to be analyzed. The sample solution generally contains a target molecule, e.g., a target nucleic acid, the presence or sequence of which is of interest to the investigator. Binding conditions will vary depending on the application and are selected in accordance with the general binding methods known including those referred to in: Maniatis et al., Molecular Cloning: A Laboratory Manual (1989), 2nd Ed., Cold Spring Harbor, N.Y. and Berger and Kimmel, Methods in Enzymology, Volume 152, Guide to Molecular Cloning Techniques (1987), Academic Press, Inc., San Diego, Calif.; Young and Davis (1983) Proc. Natl. Acad. Sci. (U.S.A.) 80: 1194, which are incorporated herein by reference. In some embodiments, the solution may contain about 1 molar of salt and about 1 to 50 nanomolar of targets. Optionally, the fluid delivery system includes an agitator to improve mixing in the cavity, which shortens the incubation period. Finally, the sample is washed with a buffer, which may be 6X SSPE buffer, to remove the unbound targets. In some embodiments, the cavity is filled with the buffer after washing the sample.

Following hybridization and appropriate rinsing/washing, the cartridged substrate may be aligned on a detection or imaging system, such as those disclosed in U.S. Pat. No. 5,143,854 (Pirrung et al.) or U.S. patent application Ser. Nos. 08/195,889, filed Feb. 10, 1994, 08/465,782, filed Jun. 6, 1995, 08/456,598, filed Jun. 1, 1995, incorporated herein by reference for all purposes. Such detection systems may take advantage of the cartridge's asymmetry (i.e., non-flush edge) by employing a holder to match the shape of the cartridge specifically. Thus, the cartridge is assured of being properly oriented and aligned for scanning. The imaging systems are capable of qualitatively analyzing the reaction between the probes and targets. Based on this analysis, sequence information of the targets is extracted.

VII. Examples

Example 1

Comparison of front-side and back-side photolysis

Two substrate wafers were stripped, silanated and photoprotected. The substrates were photolyzed through a mask having rectangular features of 50 and 100 μm on the short side, for 13 half lives of the photoprotecting group used. The first substrate was photolyzed from the back-side of the wafer, i.e., the synthesis surface was facing away from the photolyzing light source. The second substrate was photolyzed from the front-side, i.e., the synthesis surface was facing the light source and mask. Both substrates were then subjected to identical coupling reactions where a fluorescent 5' protected phosphoramidite was coupled to the surface of the substrate.

Figure 9A:
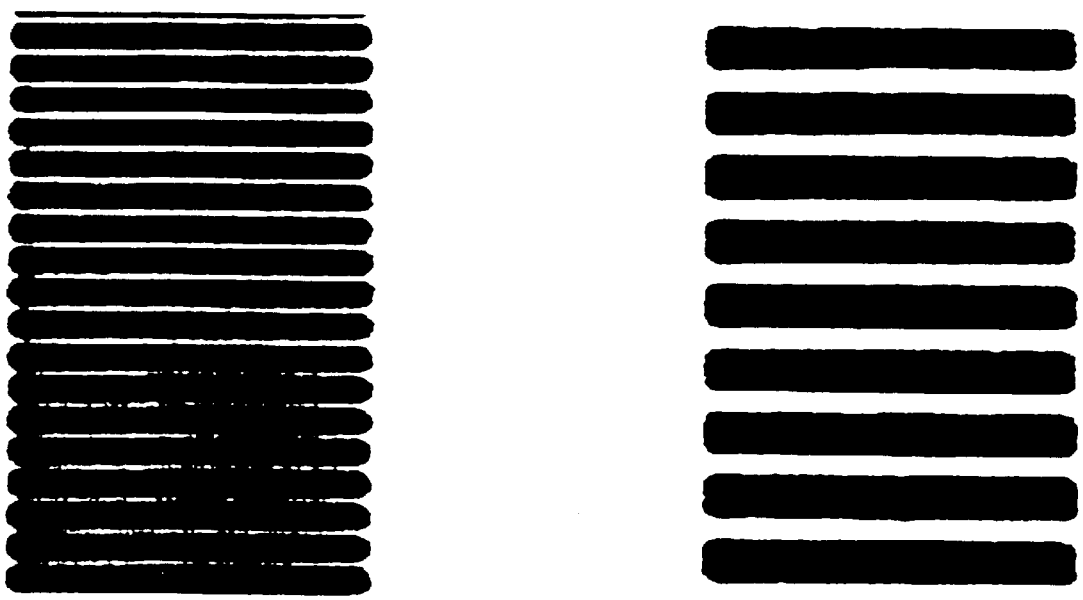
FIGS. 9A and 9B show the coupling of fluorescent nucleotides to a substrate surface using photolithographic methods in 50 and 100 μm features, using back-side and front-side exposure, respectively.
Figure 9B:
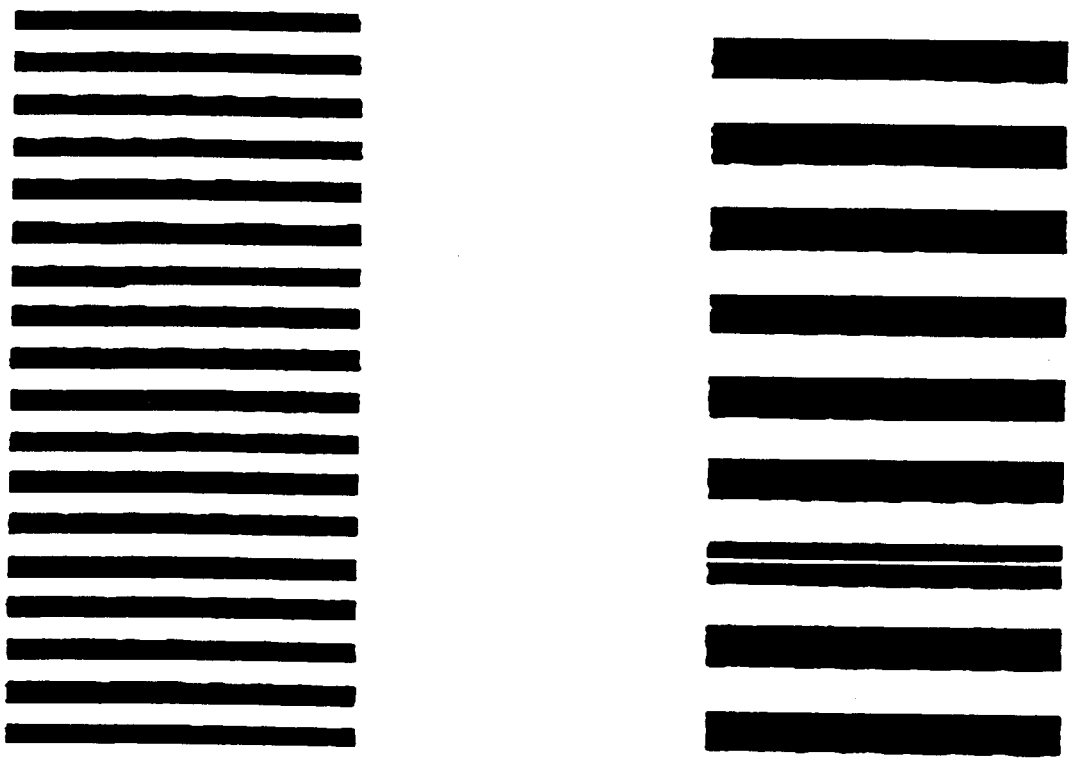

FIGS. 9A and 9B illustrate the contrast difference between back-side exposure synthesis and front-side exposure synthesis, respectively. FIG. 9A shows a fluorescent scan of a substrate having fluorescent groups coupled directly to the surface of the substrate using photolithographic techniques, with a mask having 50 μm and 100 μm feature sizes where the activating light was shown through the back-side of the substrate. FIG. 9B shows the same synthesis where the activation light was directed at the front side of the substrate. The definition of the individual features is greatly enhanced using this front-side photolysis.

Figure 9C:
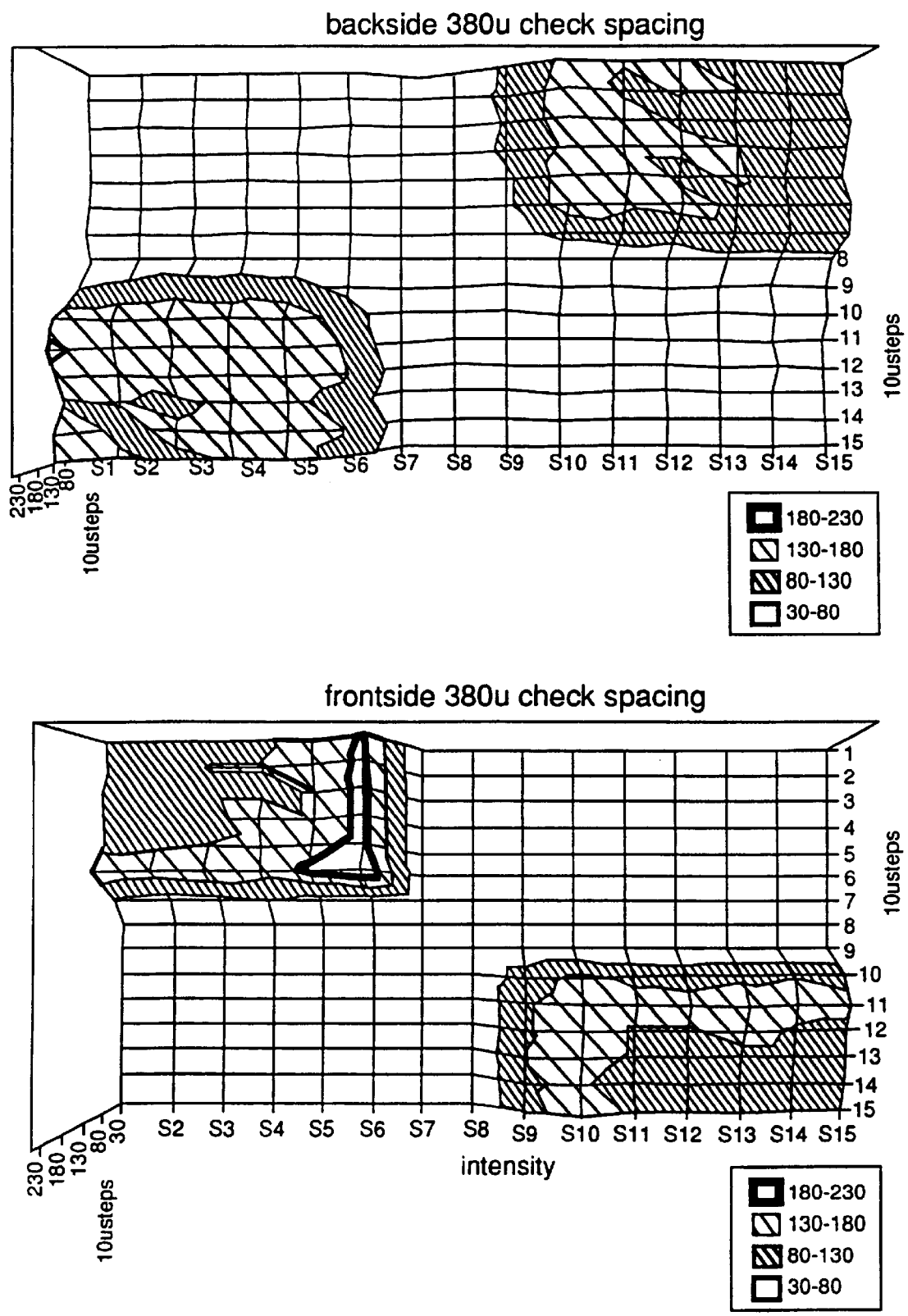
FIGS. 9C and 9D show a plot of fluorescence intensity as a function of substrate position at the border between two features for back-side and front-side exposure as indicated.
Figure 9D:
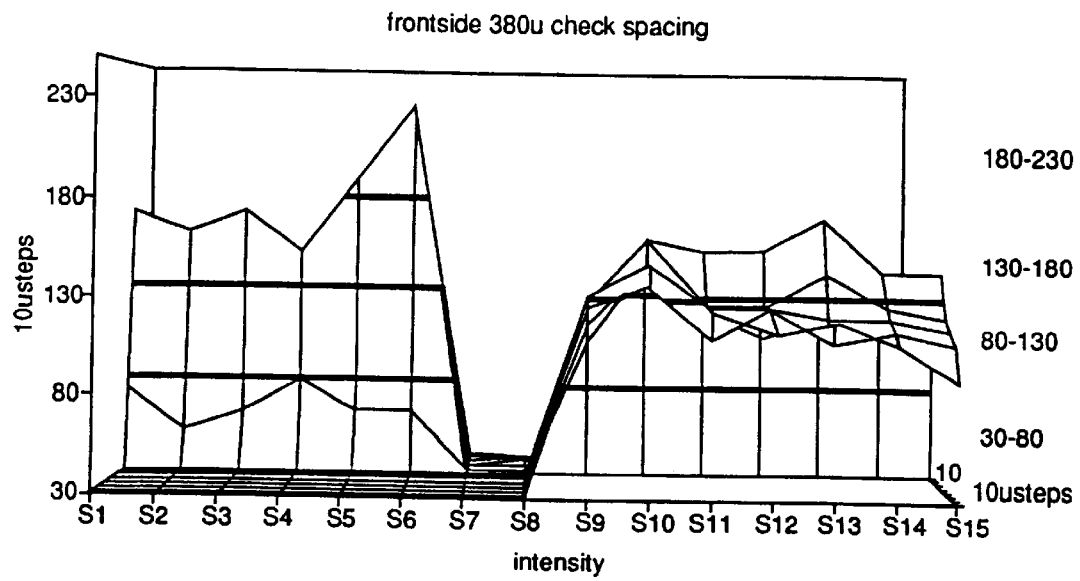
Figure 9D:
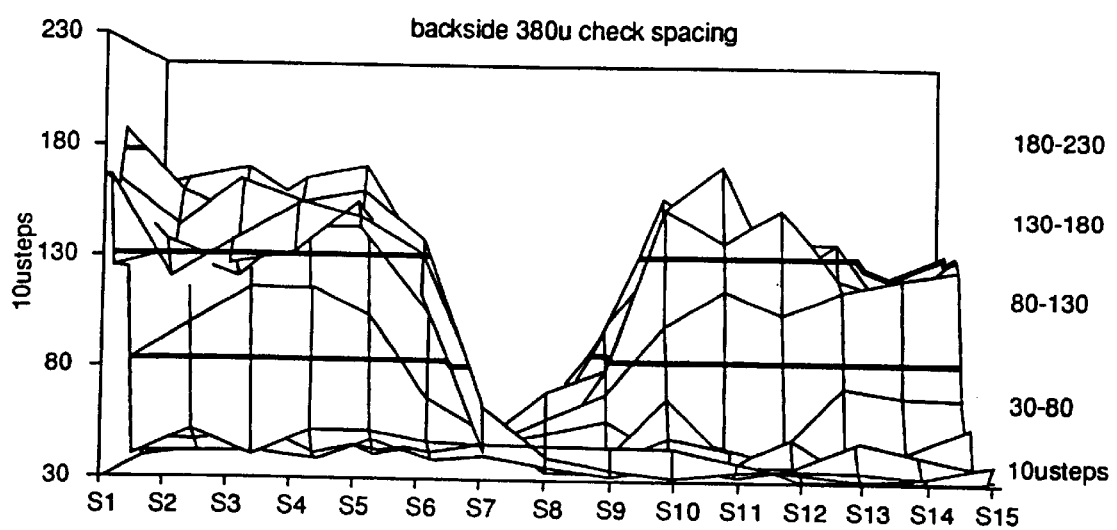

FIGS. 9C and 9D provide a graphic illustration of the differences in contrast among features prepared using back-side vs. front-side methods. Specifically, the front-side exposure provides a much sharper contrast and greater feature definition. This greater definition permits a much smaller feature size by reducing bleed-over effects during exposure. While front-side exposure results in subjecting the synthesis surface to ambient conditions during photolysis, this has not been found to have any deleterious effects on the synthesis.

Example 2

Final Deprotection with Ethanolamine and Ethylenediamine

1–8 mer oligonucleotide probes were synthesized on glass substrates derivatized with bis (2-hydroxyethyl) aminopropyltriethoxysilane, according to standard protocols. In each case, a hexaethyleneglycol-based spacer phosphoramidite was coupled to the surface before the oligonucleotide sequence, and a fluorescein-based "tag" phosphoramidite was coupled to the 5' end of the oligonucleotides, usually in a checkerboard pattern. This allowed monitoring the loss of probes from the substrates, by ascertaining a decrease in the surface fluorescence. The substrates were immersed in either concentrated aqueous ammonia or 50% ethanolic ethanolamine, or 50% ethanolic ethylenediamine in sealed containers. At specific times, the substrates were removed, washed with water, and the surface fluorescence was image was obtained, against a pH 7.2 phosphate buffer. After each scan, the substrates were washed again, dried in an inert atmosphere ($N_2$), and returned to the deprotection solution. The surface fluorescence of the substrate immersed in the aqueous ammonia deprotection solution decayed with a half-time of 8–10 hours. After two days in the ethanolic amine solutions, only a 5% decay in surface fluorescence was observed.

Example 3

Comparison of Silanation Methods and Reagents

For comparison, glass substrates were derivatized with a number of silanes using solution-phase deposition methods. Mean functional surface densities were compared by fluorescent staining. Performance with regard to oligonucleotide synthesis was compared by synthesizing a 10 mer probe sequence on the substrates, deprotecting, and hybridizing them to a standard fluorescein labelled oligonucleotide target. Standard oligonucleotide synthesis cycles (couple-cap-oxidize) were used in all cases, but were modified slightly to allow for reagent delivery to flowcells for planar substrates.

The following silanes, obtained from Huls America were tested:

3-acetoxypropyltrimethoxysilane ("OAc");

3-glycidoxypropyltrimethoxysilane ("Epoxy");

4-(hydroxybutyramido)propyltriethoxysilane ("Mono");

3-aminopropyltriethoxysilane ("APS"); and

3-N,N-bis(2-hydroxyethyl)aminopropyl triethoxysilane ("bis")

Precleaned substrates were immersed in a 1% solution of the silane in 5% water, 95% ethanol, for 5 minutes with gentle agitation. The substrates were then thoroughly rinsed with alcohol, dried under $N_2$, and cured at 100° C. for 15 minutes. Prior to use, the acetoxypropyl-silanated substrates were soaked in 50% ethanolic ethanolamine for 2 hours, then rinsed and dried. Similarly, the glycidoxypropyl-silanated substrates were soaked in 0.1 M aqueous HCl for 2 hours, rinsed then dried. All other substrates were ised withoit further treatment.

The functional group density was then measured by fluorescent staining. Specifically, MeNPOC-hexaethyleneglycol-cyanoethl phosphoramidite was coupled to the substrate and unreacvted sites were then capped with $(MeO)_2PNiPr_2$. A portion of the surface was illuminated through a photolithographic mask for 300 seconds at 365 nm (15 mW/cm$^2$) to remove the MeNPOC protecting groups. The free hydroxyls were then labeled witha fluorescein phosphoramidite (Fluoreprime™, Pharmacia Biotech). The substrate was then deprotected n 50% ethanolic ethylenediamine and surface fluorescence was measured with a scanning laser confocal microscope.

Figure 10:
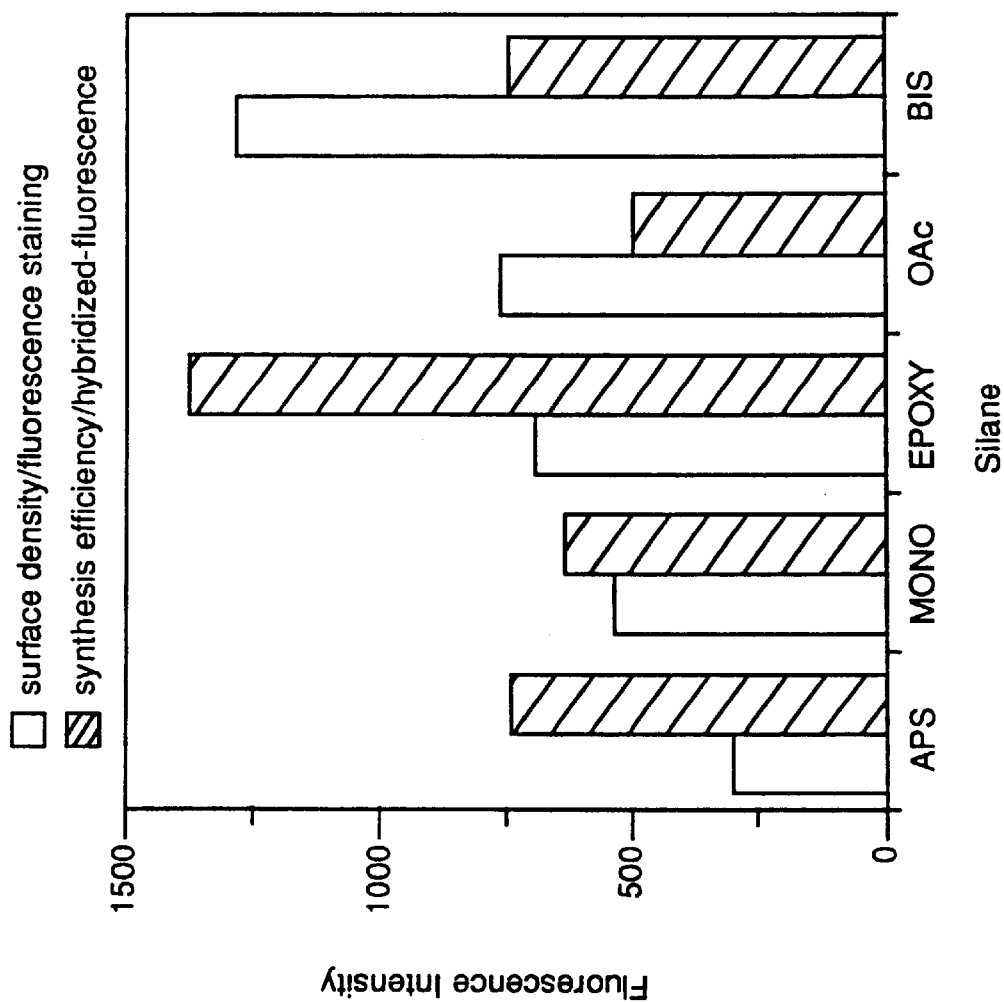
FIG. 10 is a bar chart showing a comparison of silanation methods using 5 different silanes to derivatize the surface of glass substrates (3-acetoxypropyltrimethoxysilane ("OAc"); 3-glycidoxypropyltrimethoxysilane ("Epoxy"); 4-(hydroxybutyramido)propyltriethoxysilane ("Mono"); 3-aminopropyltriethoxysilane ("APS"); and 3-N,N-bis(2-hydroxyethyl)aminopropyl; triethoxysilane ("bis")). Shown are the surface density of reactive groups as shown by fluorescence staining (black) and fluorescence intensity of a standard hybridization experiment following synthesis of oligonucleotides on the surface of substrates derivatized using these silanes (grey).

A 10 mer oligonucleotide probe sequence (5'-TACCGTTCAG-3') was synthesized on a selected region of each substrate using light-directed synthesis. After deprotection in 50% ethanolic ethylenediamine, the substrte was incubated in a solution of a complementary fluorescein-labeled oligonucleotide target (10 nM oligonucleotide in 5XSSPE buffer for 6 hours. After briefly washing the substrate once with 5XSSPE, total surface-hybridized target oligonucleotide was quantitated with a scanning laser confocal microscope. Staining and hybridization data are summarized in FIG. 10 which illustrates effective silanation of glass substrates using each of the above-described silane reagents.

Example 4

Direct transfer of protecting groups to hydroxylated substrates

Synthesis of MeNPOC-tetrazolide was carried out as follows: Tetrazole (7.0 g); 100 mmole) was combined with 17.5 ml of DIEA (13 g, 100 mmole) in 100 ml of THF, and a solution of 30 g (110 mmole) MeNPOC-chloride (See, Pease, et al, supra) in 100 ml THF was added dropwise over 20 minutes while stirring under argon at 4° C. Stirring was continued for an additional hour at room temperature. 200 ml of hexane was then added. The precipitate was collected by filtration, redissolved in 200 ml DCM and washed 3 times with 0.05 M aqueous HCl to remove DIEA-HCL. The organic layer was dried with $NaSO_4$ and evaporated to obtain 24.5 g (80%) of the pure product, which was identified by $^1$H-NMR, IR and mass spectrometry.

Figure 11:
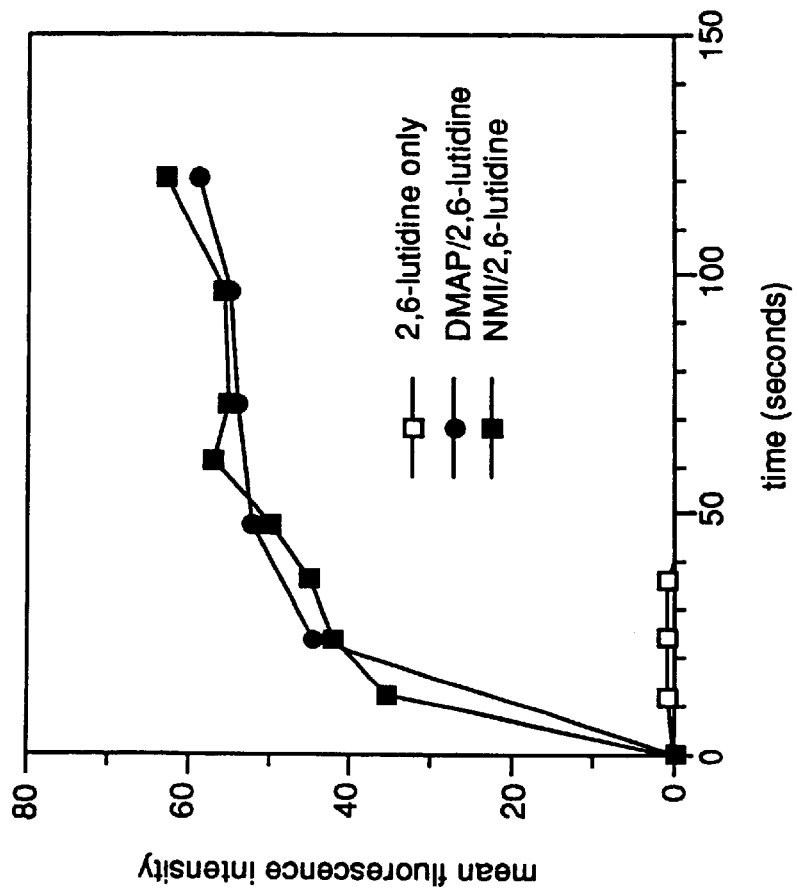
FIG. 11 shows the reprotection of deprotected hydroxyl groups on a glass substrate with MeNPOC-tetrazolide as a function of time of exposure to the MeNPOC-tetrazolide and addition of catalyst.

MeNPOC-transfer to a hydroxylated substrate with MeNPOC-tetrazolide was carried out as follows: Using methods described in the art, e.g., Pease et al., supra, hydroxylated glass substrates were prepared by silanating the glass with bis-(hydroxyethyl) aminopropyltriethoxysilane, and then adding a linker phosphoramidite (MeNPOC-hexaethyleneglycolcyanoethyl-phosphoramidite) to the substrates using a standard couple-cap-oxidize cycle. The substrates were then exposed to light (365 nm at 25 mW/cm$^2$ for 240 seconds) to remove the MeNPOC protecting groups from the linker. The free hydroxylated linker substrates were exposed to freshly mixed solutions of MeNPOC-tetrazolide (0.2M) in ACN containing 10% v/v 2,6-lutidine±5% w/v NMI or DMAP activator. After varying periods of time, the MeNPOC-tetrazolide solutions were removed and N,N-diisopropyl-dimethylphosphoramidite was added using the standard couple-cap-oxidize cycle in order to cap any unreacted hydroxyl groups. To assess the extent of MeNPOC transfer, the substrate was photolysed again, and the reexposed hydroxyls were reacted with a fluorescent phosphoramidite (Fluoreprime™, Pharmacia Biotech), added with the same couple-cap-oxidize protocol. The substrates were finally deprotected with 50% ethanolic ethanolamine and the mean surface fluorescence was measured with a laser scanning confocal microscope. FIG. 11 shows the extent of reprotection with MeNPOC tetrazolide as a function of time and catalyst.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of preparing a solid substrate for forming polymer sequences thereon, comprising:

providing functional groups on a surface of said substrate;

coupling monomers to said functional groups on said surface of said substrate, said monomers prior to coupling including lipophilic phosphoramidite groups, the lipophilic phosphoramidite groups having at least one lipophilic moiety.

2. The method according to claim 1, wherein said monomer comprises a nucleotide protected with a lipophilic protecting group.

3. A method of preparing a solid substrate for forming polymer sequences thereon, comprising:

providing functional groups on a surface of said substrate;

coupling monomers to said functional groups on said surface of said substrate. said monomers prior to coupling including lipophilic phosphoramidite groups the lipophilic phosphoramidite groups having at least one lipophilic moiety, wherein said monomer comprises a nucleotide protected with a lipophilic protecting group, wherein said lipophilic protecting group is coupled to an exocyclic functional group in a nucleobase in said nucleotide.

4. The method according to claim 3, wherein said exocyclic functional group is protected with a DMT protecting group.

5. A method of preparing a solid substrate for forming polymer sequences thereon, comprising:

providing functional groups on a surface of said substrate;

coupling monomers to said functional groups on said surface of said substrate. said monomers prior to coupling including lipophilic phosphoramidite groups, the lipophilic phosphoramidite groups having at least one lipophilic moiety, wherein said monomer comprises a nucleotide protected with a liponhilic protecting group, wherein said lipophilic protecting group is a photolabile protecting group.

6. The method according to claim 2, wherein said monomer comprises a nucleoside Fmoc-phosphoramidite.

7. A method of minimizing a number of differential synthesis steps in forming an array of polymer sequences on a surface of a substrate by sequentially deprotecting and coupling monomers in regions of said surface of said substrate to produce a plurality of different polymer sequences in different known locations of said surface of said substrate, the method comprising aligning deprotection and coupling steps in adjacent regions to minimize a number of differential synthesis steps and to optimize polymer sequence similarity between said adjacent regions.

8. A method of minimizing the number of synthetic steps in probing a target sequence by utilizing an array of polymer sequences wherein each polymer sequence has a subsequence of monomers common to a sequence that is complementary to a target sequence, but wherein at least one position within said subsequence is substituted with each member of a basis set of monomers, the method comprising coupling all monomers in a same layer of a first of said polymer sequences in a same synthesis cycle with corresponding monomers in a second of said polymer sequences.

9. An array of polymers comprising:

a substrate having a layer including one or more of an index matching material, a light absorbing material or an antireflective material and a plurality of polymers disposed on the substrate.

10. The array of claim 9 wherein the antireflective material includes a member selected from the group consisting of magnesium fluoride, polymethylmethacrylate and polyimide.

11. The array of claim 9 wherein the antireflective material includes magnesium fluoride.

12. The array of claim 9 wherein the antireflective material includes polymethylmethacrylate.

13. The array of claim 9 wherein the antireflective material includes polyimide.

14. The array of claim 9 wherein the layer has a thickness of between about 1 $\mu$m to about 50 $\mu$m.

15. The array of claim 9 wherein the layer has a thickness of between about 5 $\mu$m to about 20 $\mu$m.

16. The array of claim 9 wherein the layer has a thickness of about 10 $\mu$m.

17. The array of claim 9 wherein the layer is removable.

18. The array of claim 9 wherein the substrate is a flat substrate, a planar substrate, an aerogel, a silica aerogel, a particle, a strand, a precipitate, a gel, a sheet, a tube, a glass tube, a capillary tube, a microcapillary tube, a container, a pad, a slice, a film, a plate, or a slide.

19. The array of claim 9 wherein the polymers have known sequences and are disposed on the substrate at positionally distinct locations.

20. The array of claim 9 wherein the polymers comprise peptides or nucleic acids.

21. An array of polymers comprising:

a substrate having a layer including one or more of an index matching material, a light absorbing material or an antireflective material and a plurality of nucleic acids or peptides disposed on the substrate at positionally distinct locations.

22. The array of claim 21 wherein the substrate is a flat substrate, a planar substrate, an aerogel, a silica aerogel, a particle, a strand, a precipitate, a gel, a sheet, a tube, a glass tube, a capillary tube, a microcapillary tube, a container, a pad, a slice, a film, a plate, or a slide.

23. An array of polymers comprising:

a substrate including different polymers disposed on the substrate at positionally distinct locations and wherein the polymers have known sequences and wherein it is known which polymer is at which location, and a coating on the substrate wherein the coating is selected to match the refractive index of the substrate so as (1) to prevent refraction of light passing through the substrate during photolysis or (2) to absorb light at the wavelength of light used during photolysis to prevent back reflection.

24. The array of claim 23 wherein the polymers are peptides or nucleic acids.

25. The array of claim 9 wherein the index matching material has a refractive index approximately equal to that of the substrate.

26. The array of claim 9 wherein the index matching material has a refractive index within approximately 10% of the refractive index of the substrate.

27. The array of claim 9 wherein the index matching material has a refractive index within approximately 5% of the refractive index of the substrate.

28. The array of claim 9 wherein the index matching material has a refractive index approximately equal to that of a glass substrate.

29. The array of claim 9 wherein the light absorbing material absorbs light having a wavelength approximately equal to that of light used during photolysis.

30. The array of claim 9 wherein the light absorbing material absorbs ultraviolet light.

31. The array of claim 9 wherein the light absorbing material absorbs light within the wavelength range of about 280 nm to about 400 nm.

32. The array of claim 21 wherein the index matching material has a refractive index approximately equal to that of the substrate.

33. The array of claim 21 wherein the index matching material has a refractive index within approximately 10% of the refractive index of the substrate.

34. The array of claim 21 wherein the index matching material has a refractive index within approximately 5% of the refractive index of the substrate.

35. The array of claim 21 wherein the index matching material has a refractive index approximately equal to that of a glass substrate.

36. The array of claim 21 wherein the light absorbing material absorbs light having a wavelength approximately equal to that of light used during photolysis.

37. The array of claim 21 wherein the light absorbing material absorbs ultraviolet light.

38. The array of claim 21 wherein the light absorbing material absorbs light within the wavelength range of about 280 nm to about 400 nm.

39. An array of polymers comprising:

a substrate having a layer including a material having a refractive index within about 10% of the refractive index of the substrate and which absorbs ultraviolet light and a plurality of polymers disposed on the substrate.

40. The array of claim 39 wherein the material has a refractive index within approximately 5% of the refractive index of the substrate.

41. The array of claim 39 wherein the material has a refractive index approximately equal to that of a glass substrate.

42. The array of claim 39 wherein the material absorbs light having a wavelength approximately equal to that of light used during photolysis.

43. The array of claim 39 wherein the material absorbs ultraviolet light.

44. The array of claim 39 wherein the material absorbs light within the wavelength range of about 280 nm to about 400 nm.

45. The array of claim 9 wherein the layer is a vapor-deposited layer or a spray-applied layer.

46. A method of coating a surface of a substrate comprising coating the surface of a substrate with a curable solution of one or more of an index matching material, a light absorbing material or an antireflective material;

heating the substrate at a first temperature for a first period of time, then heating the substrate at a second temperature higher than the first temperature and for a second period of time longer than the first period of time in a manner to form a cured layer of an index matching material, a light absorbing material or an antireflective material.

47. The method of claim 46 wherein the first temperature is about 85° C.

48. The method of claim 46 wherein the first time period is about 5 minutes.

49. The method of claim 46 wherein the second temperature is between about 220° C. and 360° C.

50. The method of claim 46 wherein the second time period is about 60 minutes.

51. The method of claim 46 wherein the curable solution is coated onto the substrate by vapor deposition.

52. The method of claim 46 wherein the curable solution is coated onto the substrate by spray application.

* * * * *

UNITED STATES PATENT AND TRADEMARK OFFICE
CERTIFICATE OF CORRECTION

PATENT NO. : 6,706,875 B1
DATED : March 16, 2004
INVENTOR(S) : Martin Goldberg et al.

It is certified that error appears in the above-identified patent and that said Letters Patent is hereby corrected as shown below:

<u>Title page,</u>
Item [73], Assignee's name should be corrected as follows:
-- Affymetrix, Inc. --

Signed and Sealed this

First Day of June, 2004

JON W. DUDAS
*Acting Director of the United States Patent and Trademark Office*